US006248878B1

(12) United States Patent
Matulic-Adamic et al.

(10) Patent No.: US 6,248,878 B1
(45) Date of Patent: *Jun. 19, 2001

(54) NUCLEOSIDE ANALOGS

(75) Inventors: Jasenka Matulic-Adamic, Boulder; Leonid Beigelman, Longmont; Alexander Karpeisky, Lafayette, all of CO (US)

(73) Assignee: Ribozyme Pharmaceuticals, Inc., Boulder, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 08/975,238

(22) Filed: Nov. 21, 1997

Related U.S. Application Data
(60) Provisional application No. 60/034,444, filed on Dec. 24, 1996.

(51) Int. Cl.[7] ............................................. C07H 7/06
(52) U.S. Cl. ................... 536/29.2; 536/26.26; 536/26.8; 536/28.1; 514/42; 514/43; 514/44
(58) Field of Search .................. 536/26.26, 26.6, 536/26.8, 26.74, 27.21, 27.6, 27.8, 27.81, 28.1, 28.5, 28.53, 28.54, 23.1, 29.2; 935/33, 34, 69.1; 435/6, 91.11, 72.1, 240, 240.2, 375, 325; 514/43, 44, 45, 46, 47, 48, 49, 50, 51, 92

(56) References Cited

U.S. PATENT DOCUMENTS

| | | |
|---|---|---|
| 4,987,071 | 1/1991 | Cech et al. . |
| 5,134,066 | 7/1992 | Rogers et al. . |
| 5,334,711 | 8/1994 | Sproat et al. . |
| 5,420,266 * | 5/1995 | Britton et al. .................. 536/28.5 |
| 5,672,501 * | 9/1997 | Matulic-Adamic et al. . |
| 5,783,425 * | 7/1998 | Dodycz et al. .................. 536/23.1 |

FOREIGN PATENT DOCUMENTS

| | | |
|---|---|---|
| B-86139/91 | 5/1994 | (AU) . |
| 2165971 | 12/1995 | (CA) . |
| 0 227 844 A1 | 7/1987 | (EP) . |
| 0 227 844 B1 | 7/1987 | (EP) . |
| 0 360 257 A2 | 3/1990 | (EP) . |
| 93/12130 | 6/1993 | (WO) . |
| 93/15187 | 8/1993 | (WO) . |
| 93/23569 | 11/1993 | (WO) . |
| 94/02595 | 2/1994 | (WO) . |
| 95/01363 | 1/1995 | (WO) . |
| 95/11304 | 4/1995 | (WO) . |
| 95/11910 | 5/1995 | (WO) . |
| 95/13378 | 5/1995 | (WO) . |
| 95/23225 | 8/1995 | (WO) . |
| 96/18736 | 6/1996 | (WO) . |
| 96/22689 | 8/1996 | (WO) . |

OTHER PUBLICATIONS

Biochemistry, vol. 35, No. 45, pp. 14090–14097. (1996).*
Tetrahedron Letters, vol. 38, No. 2, pp. 203–206 (1997).*
Belmans et al. "Synthesis and Biological Evaluation of a Series of Substituted Pyridine–C–Nucleosides. Part V: 3–Chloro–4–(D–Ribofuranosyl) Pyridine and 3–(D–Ribofuranosyl)–2–Pyridone" *Nucleosides & Nucleotides* 8(3):307–315 (1989).
Cech, "Ribozymes and Their Medical Implications," *JAMA* 260:3030–3034 (1988).
Chowrira et al., "Extensive Phosphorothioate Substitution Yields Highly Active and Nuclease–Resistant Hairpin Ribozymes," *Nucleic Acids Research* 20:2835–2840 (1992).
Christoffersen et al., "Ribozymes as Human Therapeutic Agents," *J. Med. Chem.* 38:2023–2037 (1995).
Dondoni, A. et al., "Thiazole–Based Synthesis of Formyl C–Glycosides" *J. Org. Chem.*, 59: 6404–6412 (1994).
Duval–Valentin et al., "Specific Inhibition of Transcription by Triple Helix–Forming Oligonucleotides," *Proc. Natl. Acad. Sci. USA* 89:504–508 (1992).
Egholm et al., "PNA Hybridizes to Complementary Oligonucleotides Obeying the Watson–Crick Hydrogen–Bonding Rules," *Nature* 365:566–568 (1993).
Feldstein et al., "Two Sequences Participating in the Autolytic Processing of Satellite Tobacco Ringspot Virus Complementary RNA," *Gene* 82:53–61 (1989).
Forster et al., "External Guide Sequences for an RNA Enzyme," *Science* 249:783–786 (1990).
Gudmundsson et al., "The Condensation of 2,6–Dichloroimidazo[1,2–a] pyridine with Ribonolactone Gives a Novel Imidazo [1,2–a] pyridine C–nucleoside with an Unexpected Site of Ribosylation" *Tetrahedron Lett.* 37:2365–2368 (1996).
Guerrier–Takada et al., "The RNA Moiety of Ribonuclease P Is the Catalytic Subunit of the Enzyme," *Cell* 35:849–857 (1983).
Hakimelahi et al. "New Catalysts and Procedures for the Dimethoxytritylation and Seletive Silylation of Ribonucleosides" *Can. J. Chem.* 60: 1106–1113 (1982).
Hama et al., "Preparation and Properties of Pyridine–Analogue of TCNQ Dianion Salt" *Bull. Chem. Soc. Jpn.* 61: 1683–1686 (1988).

(List continued on next page.)

*Primary Examiner*—James O. Wilson
(74) *Attorney, Agent, or Firm*—McDonnell Boehnen Hulbert & Berghoff

(57) ABSTRACT

Novel nucleoside analogs, such as 3-(β-D-Ribofuranosyl)-2-fluoropyridine, 3-(β-D-Ribofuranosyl)-pyridin-2-one, 3-(β-D-Ribofuranosyl)-pyridin-2-(4-nitrophenylethyl)-one, 3-(α-D-Ribofuranosyl)-2-fluoropyridine, 5-(β-D-Ribofuranosyl)-2-bromopyridine, 5-(α-D-Ribofuranosyl)-2-bromopyridine, 5-(β-D-Ribofuranosyl)-pyridin-2-one, 5-(α-D-Ribofuranosyl)-pyridin-2-one, 5-(β-D-Ribofuranosyl)-2-aminopyridine, 5-(β-D-Ribofuranosyl)-pyridin-2-(4-nitrophenylethyl)-one, and 5-(α-D-Ribofuranosyl)-2-aminopyridine; process for their synthesis and incorporation into polynucleotides.

16 Claims, 16 Drawing Sheets

OTHER PUBLICATIONS

Hampel et al., "'Hairpin' Catalytic RNA Model: Evidence for Helices and Sequence Requirement for Substrate RNA," *Nucleic Acids Research* 18:299–304 (1990).

Harusawa et al., "Efficient and β–Stereoselective Synthesis of 4(5)–β–D–Ribofuranosyl)–and 4(5)–(2–Deoxyribofuranosyl) imidazoles" *J. Org. Chem.* 61: 4405–4411 (1996).

Haseloff et al., "Sequences Required for Self–catalysed Cleavage of the Satellite RNA of Tobacco Ringspot Virus," *Gene* 82:43–52 (1989).

Haseloff et al., "Simple RNA Enzymes with New and Highly Specific Endoribonuclease Activities," *Nature* 334:585–591 (1988).

Hertel et al., "Numbering System for the Hammerhead," *Nucleic Acids Research* 20:3252 (1992).

Jeffries et al., "A Catalytic 13–mer Ribozyme," *Nucleic Acids Research* 17:1371–1377 (1989).

Kim et al., "Three–dimensional Model of the Active Site of the Self–splicing rRNA Precursor of *Tetrahymena*," *Proc. Natl. Acad. Sci. USA* 84:8788–8792 (1987).

Li et al., "Cleavage of RNase P of gene N mRNA reduces bacteriophage λ burst size," *Nucleic Acids Research* 24:835–842 (1996).

Limbach et al., "Summary: The Modified Nucleosides of RNA," *Nucleic Acids Research* 22(12):2183–2196 (1994).

Liu et al., "Synthesis of Pyrazine C–Ribosides via Direct Metalation" *Tetrahedron Lett.*, 37: 5325–5328 (1996).

Michels et al., "Conversion of a Group II Intron into a New Multiple–Turnover Ribozyme that Selectively Cleaves Oligonucleotides: Elucidation of Reaction Mechanism and Structure/Function Relationships," *Biochemistry* 34:2965–2977 (1995).

Milligan et al., "Synthesis of Small RNAs Using T7 RNA Polymerase," *Methods Enzymol.* 180:51–62 (1989).

Niedballa et al., "A General Synthesis of N–Glycosides. IV. Synthesis of Nucleosides of Hydroxy and Mercapto N–Heterocycles" *J. Org. Chem.* 39: 3668–3671 (1974).

Pankiewicz et al., "Efficient Synthesis of 5–(β–D–Ribofuranosyl) nicotinamide and Its α–Isomer" *J. Org. Chem.* 53: 3473–3479 (1988).

Parham et al., "Selective Halogen–Lithium Exchange in 2,5–Dibromobenzenes and 2,5–Dibromopyridine" *J. Org. Chem.* 42: 257–260 (1977).

Perreault et al., "Mixed Deoxyribo– and Ribo–Oligoneucleotides with Catalytic Activity" *Nature* 344:565–567 (1990).

Perrotta et al., "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Rossi et al., "Ribozymes as Anti–HIV–1 Therapeutic Agents: Principles, Applications, and Problems," *Aids Research and Human Retroviruses* 8:183–189 (1992).

Saville et al., "A Site–Specific Self–Cleavage Reaction Performed by a Novel RNA In Neurospora Mitochondria," *Cell* 61:685–696 (1990).

Scaringe et al., "Chemical Synthesis of Biologically Active Oligoribonucleotides Using B–cyanoethyl Protected Ribonucleoside Phosphoramidites," *Nucl Acids Res.* 18:5433–5441 (1990).

Sokolova et al., 3–β–D Ribofuranosylindoles (Indole C–Nucleosides) *Carbohydr. Res.* 93: 19–34 (1981).

Soloman et al., "Stereocontrolled Synthesis of C–Linked Deoxyribosides of 2–Hydroxypyridine and 2–Hydroxyquinoline" *Tetrahedron Lett.* 32: 3297–3300 (1991).

Soloman et al., "Chemical Synthesis and Characterization of Duplex DNA Containing a New Base Pair: A Nondisruptive, Benzofused Pyrimidine Analog" *J. Org. Chem.* 58: 2232–2243 (1993).

Stein et al., "Antisense Oligonucleotides as Therapeutic Agents—Is the Bullet Really Magical?" *Science* 261:1004–1288 (1993).

Szarek et al., "Synthesis of Nucleosides by Direct Replacement of the Anomeric Hydroxy–group" *J.C.S. Chem. Comm.* (1975).

Tam et al., "Nucleosides. 113. Synthesis of 6–(β–D–Ribofuranosyl) pyrimidines. A New Class of Pyrimidine C–Nucleosides [1,2]" *J. Org. Chem.* 44: 4854–4862 (1979).

Torrence et al., "Targeting RNA for Degradation with a (2'–5') Oligoadenylate–antisense Chimera," *Proc. Natl. Acad. Sci. Usa* 90:1300–1304 (1993).

Tuschl et al., "Importance of Exocyclic Base Functional Groups of Central Core Guanosines for Hammerhead Ribozyme Activity," *Biochemistry* 32:11658–11668 (1993).

Uhlenbeck, "A Small Catalytic Oligoribonucleotide," *Nature* 328:596–600 (1987).

Uhlmann et al., "Antisense Oligonucleotides: A New Therapeutic Principle," *Chemical Reviews* 90:544–584 (1990).

Usman et al., "Exploiting the Chemical Synthesis of RNA," *TIBS* 17:334–339 (1992).

Usman et al., "Ch. 30—Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethionine tRNA," *J. Am. Chem. Soc.* 109:7845–7854 (1987).

Wincott et al., "Synthesis, Deprotection, Analysis and Purification of RNA and Ribozymes," *Nucleic Acids Research* 23:2677–2684 (1995).

Yokoyama et al., "Synthesis of C–Ribo–Nucleosides Having Typical Aromatic Heterocycles as Base Moiety" *Chem. Lett.* 265–268 (1994).

Zaug et al., "The Tetrahymena Ribozyme Acts Like an RNA Restriction Endonuclease," *Nature* 324:429–433 (1986).

Burgess et al., "Synthesis of an oxyamide linked nucleotide dimer and incorporation into antisense oligonucleotide sequences," *J. Chem. Soc. Chem. Commun.* pp. 915–916 (1994).

Perbost et al., "Synthesis of 5'–O–Amino–2'– deoxypyrimidine and purine nucleosides: Building blocks for antisense oligonucleosides," *J. Org. Chem.* 60:5150–5156 (1995).

* cited by examiner

*Figure 1. Hammerhead Ribozyme*

Figure 2. Hammerhead Ribozyme Substrate Motifs

Figure 3. Hairpin Ribozyme

Figure 4. Hepatitis Delta Virus (HDV) Ribozyme

Figure 5. Neurospora VS Ribozyme

Figure 6: Novel Nucleoside Analogs

5-(β-D-Ribofuranosyl)-Pyridin-2-One Monomer

Reagents and Conditions: i: Et₃SiH/BF₃•Et₂O/CH₃CN, 0 °C–rt, 2.5 h, ii: 1 M TBAF/THF, 45 min, iii: 80% aq. CH₃COOH, reflux, 1.5 h, iv: TMSI, CH₂Cl₂, rt, 4 h, v: Ac₂O/DMAP/TEA/CH₃CN, 1 h, vi: Et₃SiH/BF₃•Et₂O/CH₂Cl₂, 0 °C–rt, 20 min, vii: KH/BnOH/DMF, 140 °C.

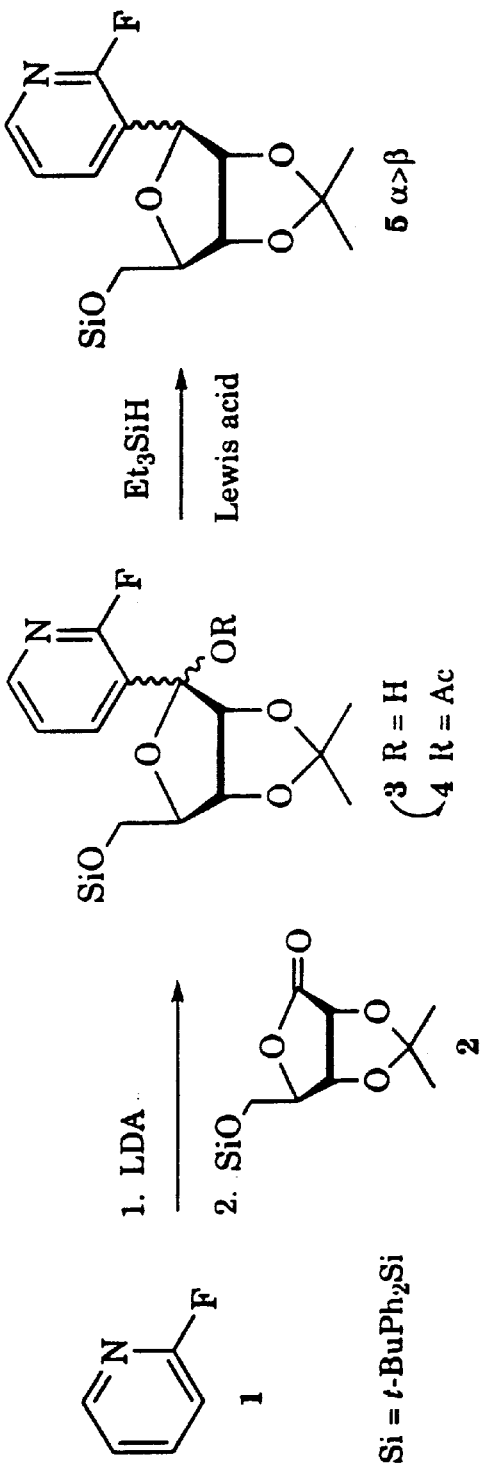
*Figure 8A: 3-(β-D-ribofuranosyl)-2-Fluoropyridine and 3-(β-D-ribofuranosyl)-Pyridin-2-one Monomer*

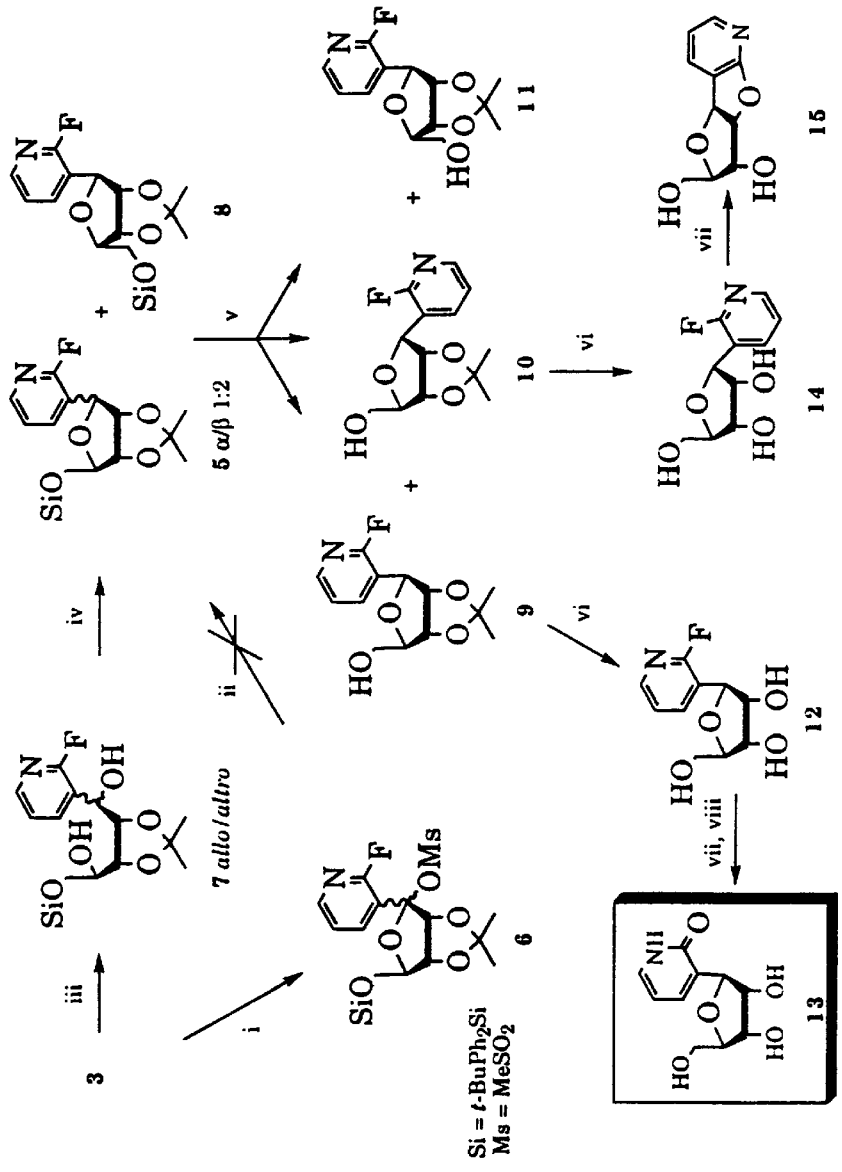
Figure 8B: 3-(β-D-ribofuranosyl)-2-Fluoropyridine and 3-(β-D-ribofuranosyl)-Pyridin-2-one Monomer

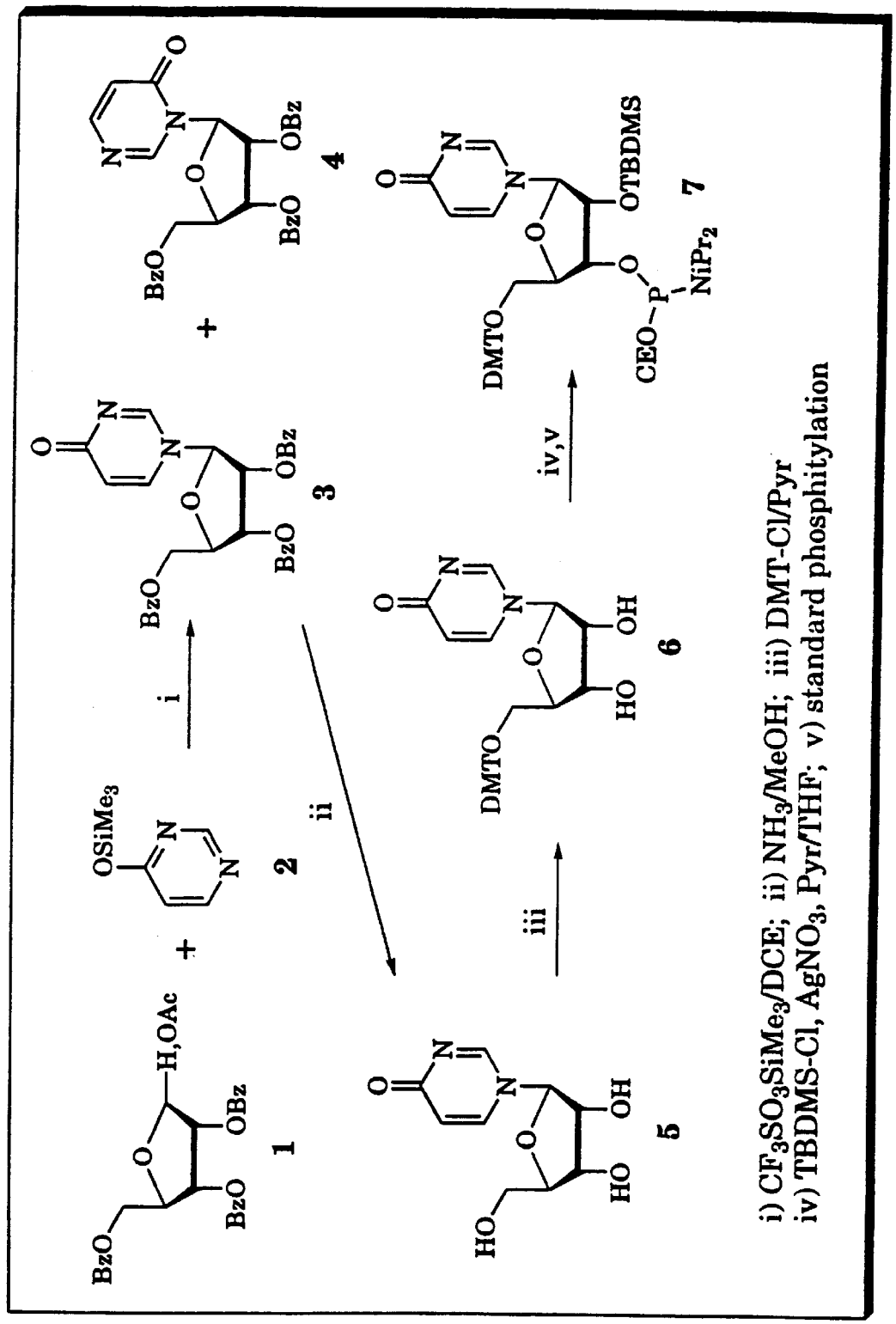
*Figure 9: Pyrimidine-4-one Monomer*

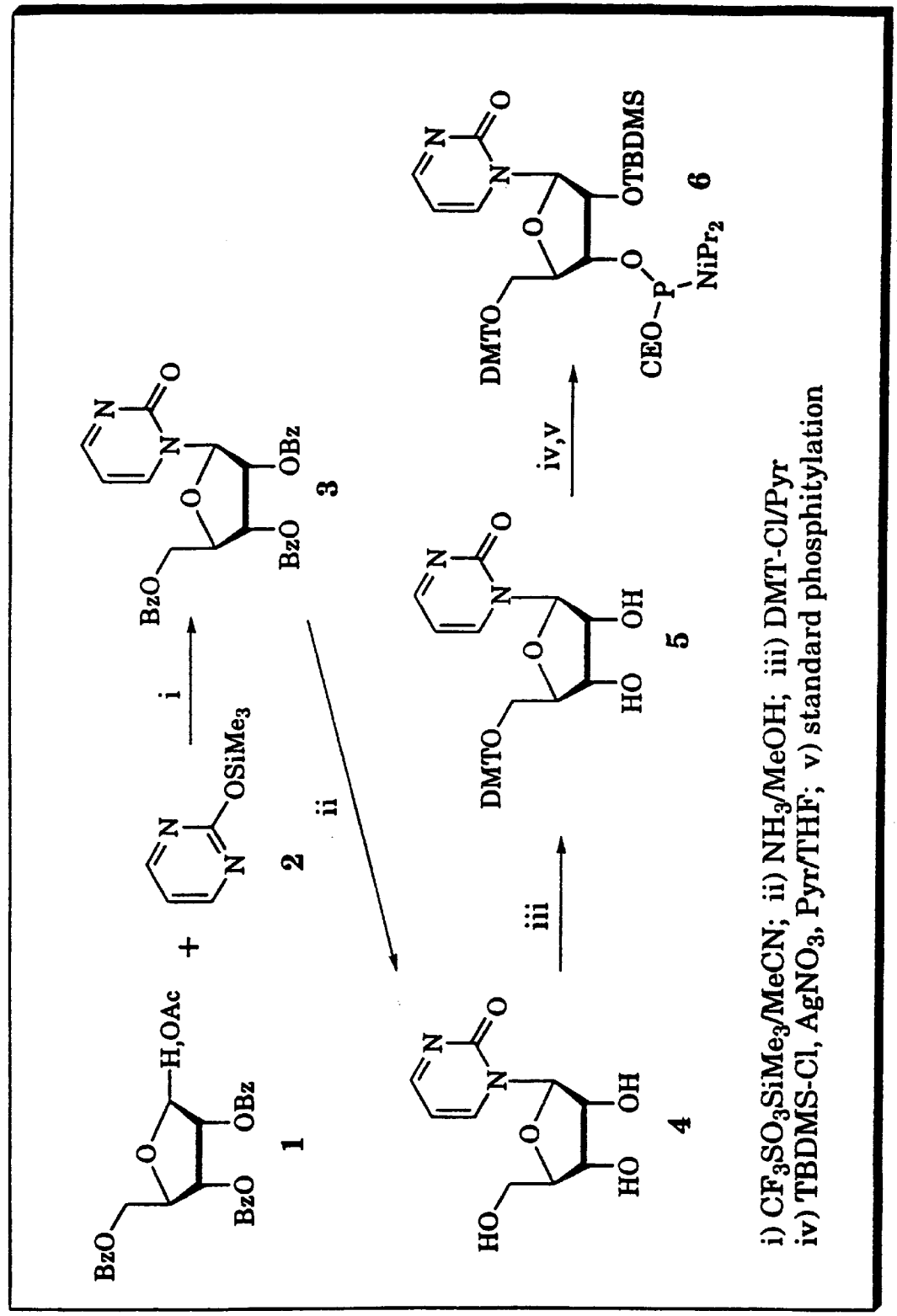
Figure 10: Pyrimidine-2-one Monomer
i) $CF_3SO_3SiMe_3$/MeCN; ii) $NH_3$/MeOH; iii) DMT-Cl/Pyr
iv) TBDMS-Cl, $AgNO_3$, Pyr/THF; v) standard phosphitylation

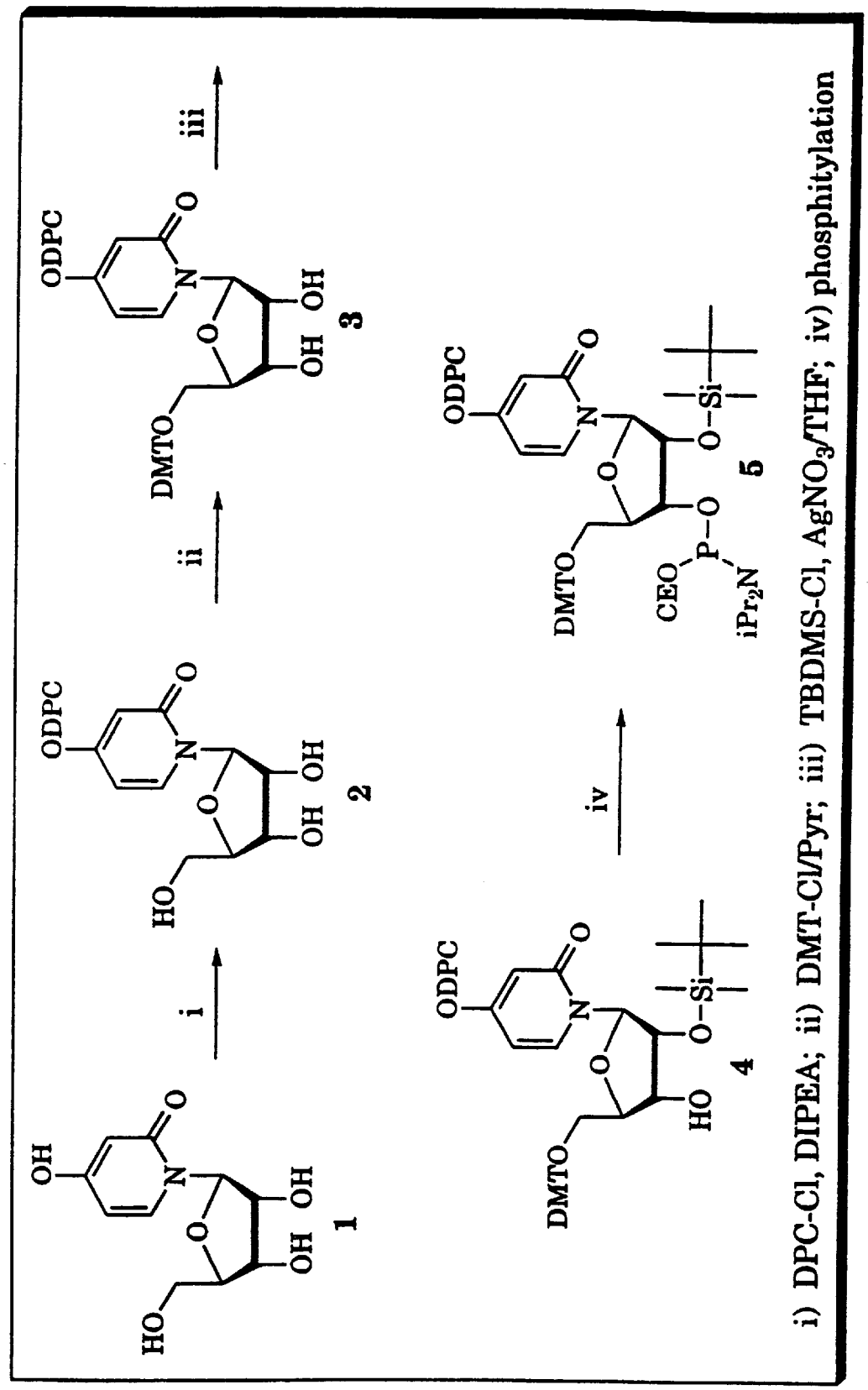
*Figure 11: 3-Deaza Uridine Phosphoramidite*
i) DPC-Cl, DIPEA; ii) DMT-Cl/Pyr; iii) TBDMS-Cl, AgNO₃/THF; iv) phosphitylation

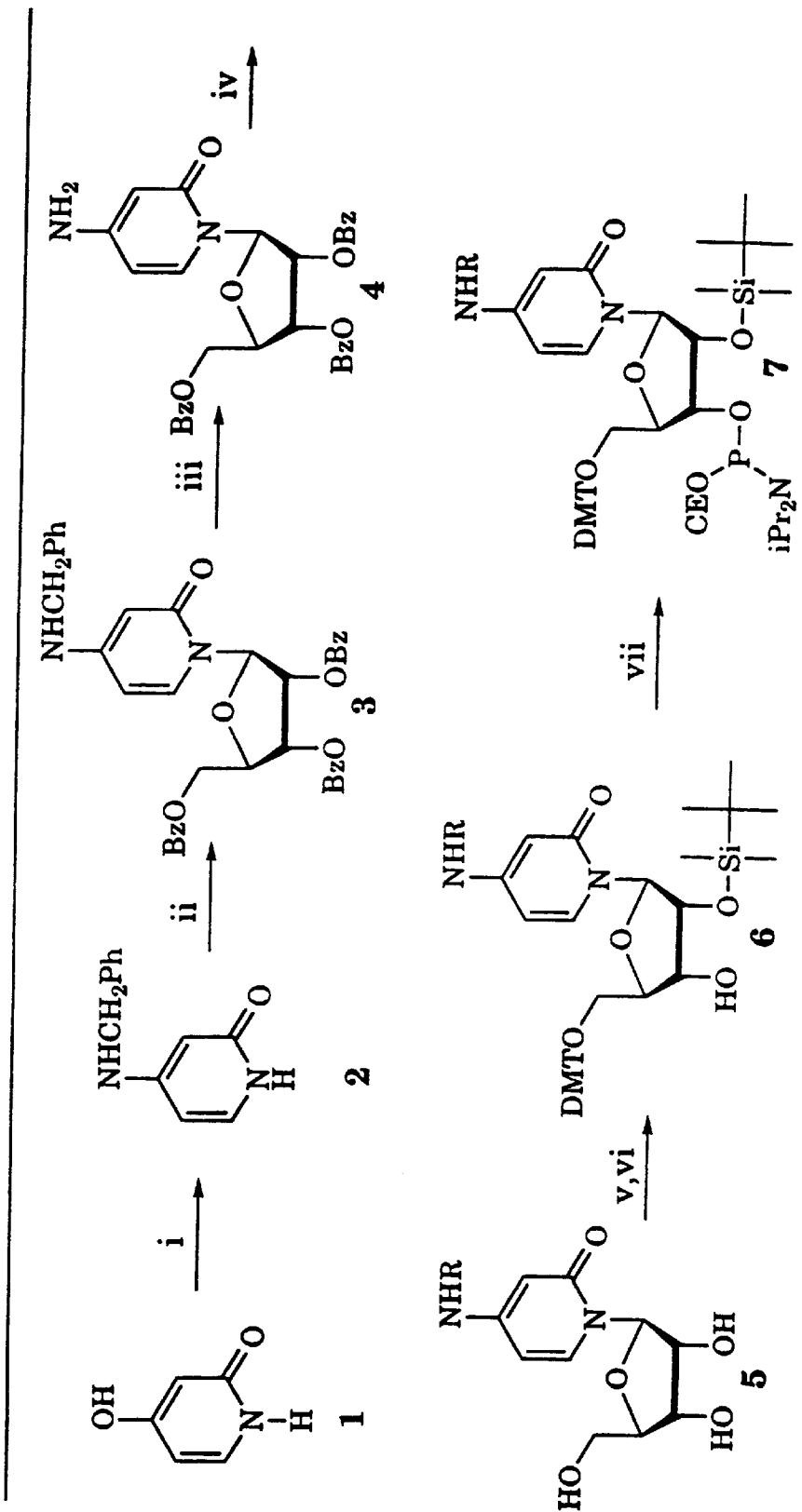
Figure 12: 3-Deaza Cytidine Phosphoramidite
i) PhCH$_2$NH$_2$, boiling; ii) glycosylation; iii) hydrogenolysis; iv) introduction of appropriate protection (Ac, TFA, DMF), then 2M NaOH; v) DMT-Cl; vi) TBDMS-Cl, AgNO$_3$/THF; vii) phosphitylation

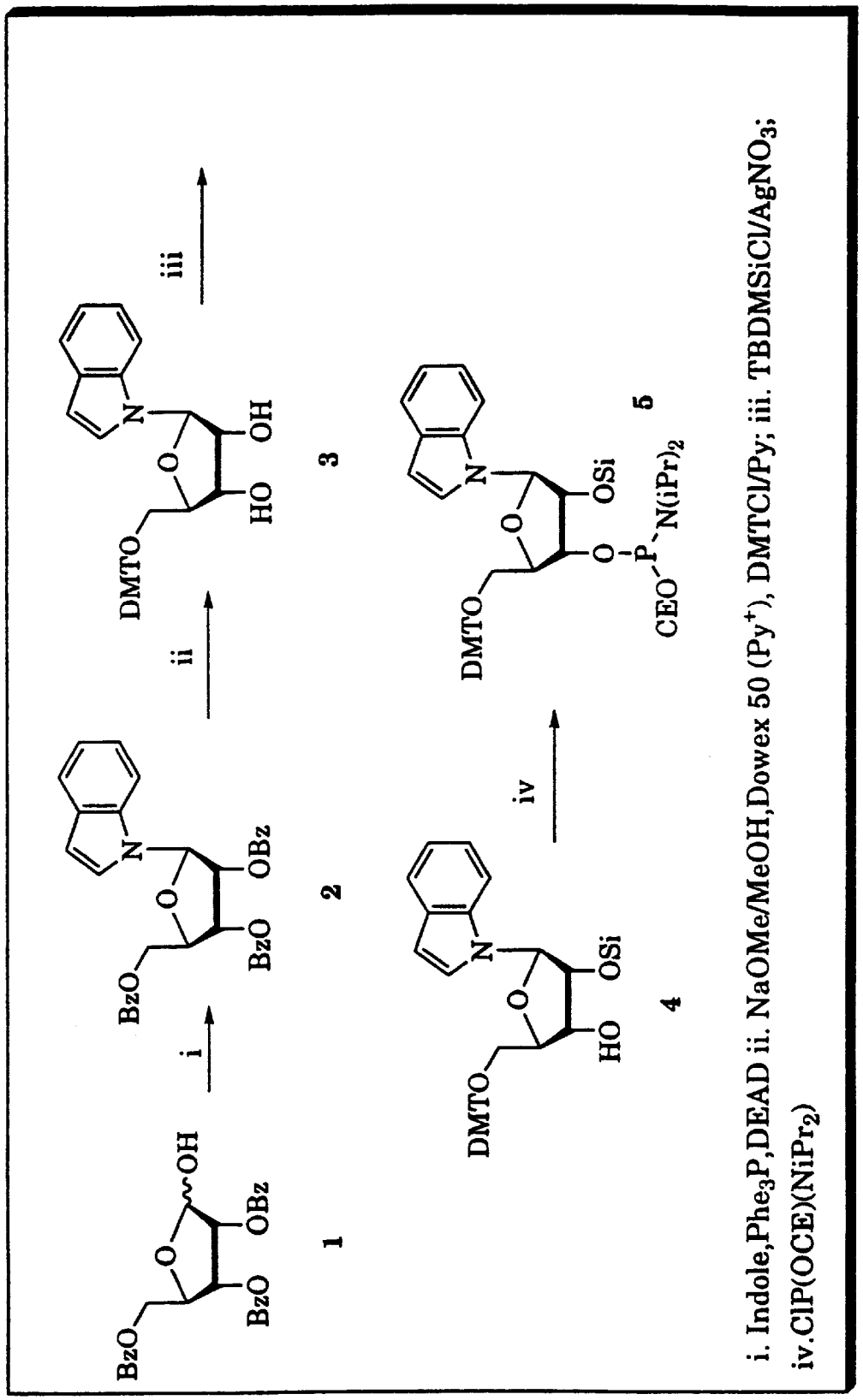
*Figure 13: Indole Phosphoramidite*

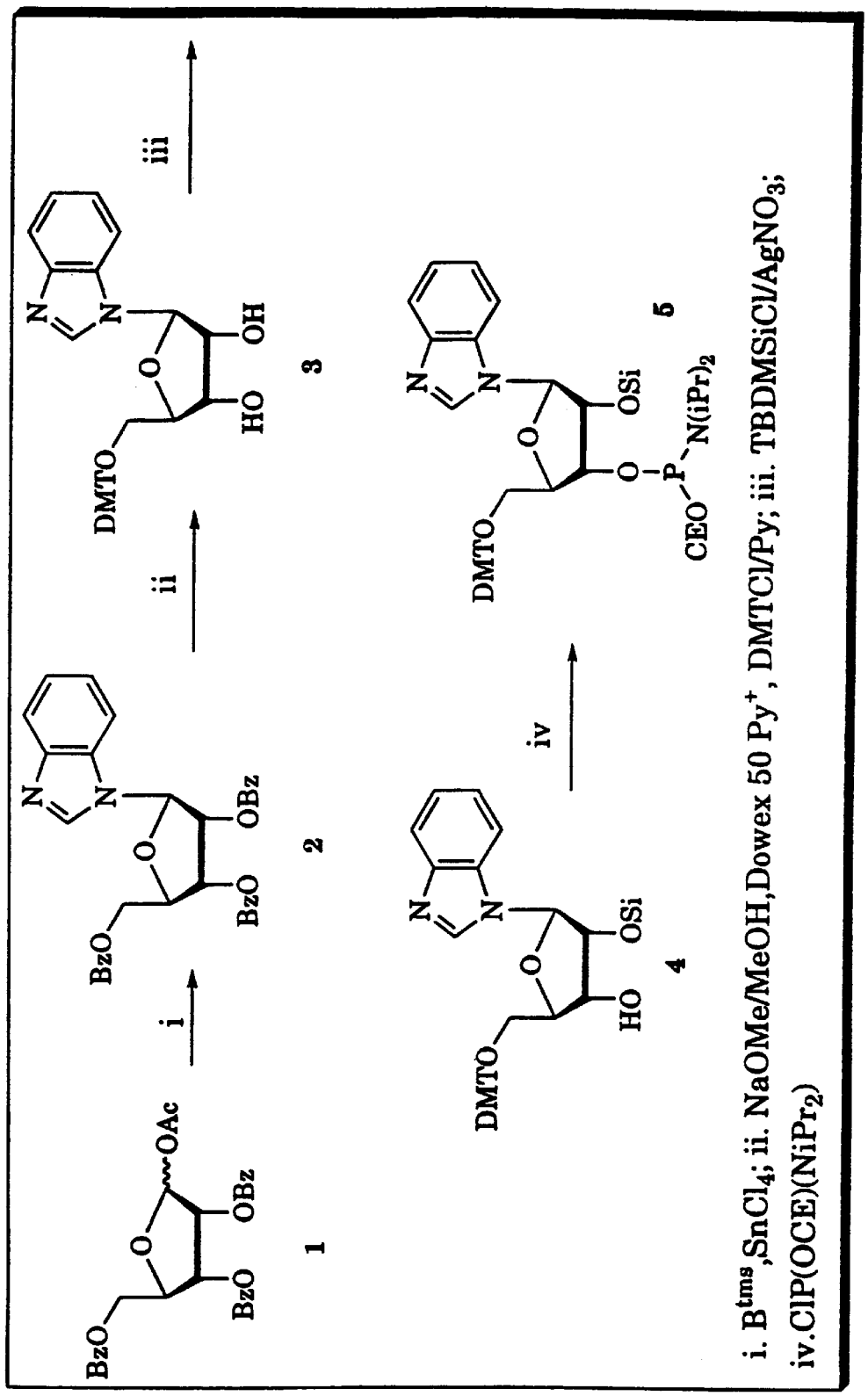
*Figure 14: Benzimidazole Phosphoramidite*

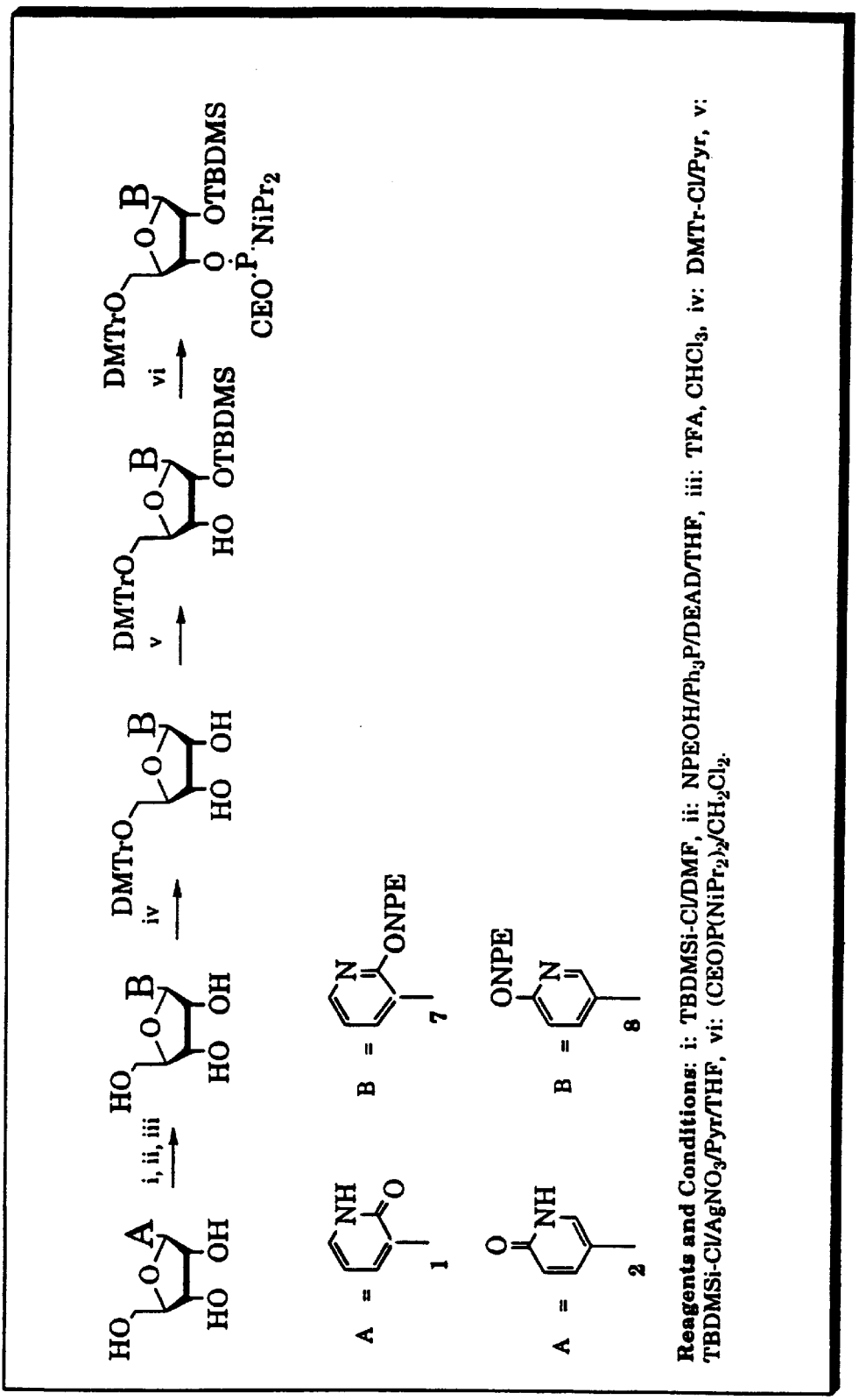
Figure 15: 3-(β-D-Ribofuranosyl)-Pyridine-2-(4-Nitrophenylethyl)-One and 5-(β-D-Ribofuranosyl)-Pyridine-2-(4-Nitrophenylethyl)-One Phosphoramidite

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
      (A) LENGTH: 11 base pairs
      (B) TYPE: nucleic acid
      (C) STRANDEDNESS: single
      (D) TOPOLOGY: linear (ix) FEATURE:
      (D) OTHER INFORMATION: The letter "N" stands for any base.
          The letter "H" stands for A, C or U.

(xi) SEQUENCE DESCRIPTION: SEQ ID NO: 1:

NNNNUHNNNN N                                            11

(2) INFORMATION FOR SEQ ID NO: 2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ix) FEATURE:
      (D) OTHER INFORMATION: The letter "N" stands for any base.

(xi) SEQUENCE DESCRIPTION: SEQ ID NO: 2:

NNNNNCUGAN GAGNNNNNNC GAAANNNN                     28

(2) INFORMATION FOR SEQ ID NO: 3:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ix) FEATURE:
      (D) OTHER INFORMATION: The letter "N" stands for any base.
          The letter "Y" is stands for C or U.
          The letter "H" stands for A, C or U.

(xi) SEQUENCE DESCRIPTION: SEQ ID NO: 3:

NNNNNNNYNG HYNNN                                     15

(2) INFORMATION FOR SEQ ID NO: 4:

(i) SEQUENCE CHARACTERISTICS:
      (A) LENGTH: 47 base pairs
      (B) TYPE: nucleic acid
      (C) STRANDEDNESS: single
      (D) TOPOLOGY: linear (ix) FEATURE:
      (D) OTHER INFORMATION: The letter "N" stands for any base.
          The letter "H" stands for A, C or U.

(xi) SEQUENCE DESCRIPTION: SEQ ID NO: 4:

NNNNGAAGNN NNNNNNNNNA AAHANNNNNN NACAUUACNN NNNNNNN      47

(2) INFORMATION FOR SEQ ID NO: 5:

(i) SEQUENCE CHARACTERISTICS:

```
        (A) LENGTH:            49 base pairs
        (B) TYPE:              nucleic acid
        (C) STRANDEDNESS:      single
        (D) TOPOLOGY:          linear (xi) SEQUENCE DESCRIPTION: SEQ ID NO: 5:

CUCCACCUCC UCGCGGUNNN NNNNGGGCUA CUUCGGUAGG CUAAGGGAG           49

(2) INFORMATION FOR SEQ ID NO: 6:

(i) SEQUENCE CHARACTERISTICS:
        (A) LENGTH:            176 base pairs
        (B) TYPE:              nucleic acid
        (C) STRANDEDNESS:      single
        (D) TOPOLOGY:          linear (xi) SEQUENCE DESCRIPTION: SEQ ID NO: 6:

GGGAAAGCUU GCGAAGGGCG UCGUCGCCCC GAGCGGUAGU AAGCAGGGAA CUCACCUCCA    60

AUUUCAGUAC UGAAAUUGUC GUAGCAGUUG ACUACUGUUA UGUGAUUGGU AGAGGCUAAG    120

UGACGGUAUU GGCGUAAGUC AGUAUUGCAG CACAGCACAA GCCCGCUUGC GAGAAU        176
```

NUCLEOSIDE ANALOGS

CROSS REFERENCE TO RELATED APPLICATIONS

This application claims the benefit of Jasenka Matulic-Adamic et al, U.S. Provisional Application No. 60/034,444, entitled "Novel Nucleoside Analogs", filed Dec. 24, 1996, which is hereby incorporated herein by reference in its entirety, including any drawings and figures.

BACKGROUND OF THE INVENTION

This invention relates to novel nucleoside analogs, processes for their synthesis and incorporation into polynucleotides.

The following is a brief description of nucleoside analogs. This summary is not meant to be complete but is provided only for an understanding of the invention that follows. This summary is not an admission that all of the work described below is prior art to the claimed invention.

Nucleoside modifications of bases and sugars, have been discovered in a variety of naturally occurring RNA (e.g., tRNA, mRNA, rRNA; reviewed by Hall, 1971 *The Modified Nucleosides in Nucleic Acids,* Columbia University Press, New York; Limbach et al., 1994 *Nucleic Acids Res.* 22, 2183). In an attempt to understand the biological significance, structural and thermodynamic properties, and nuclease resistance of these nucleoside modifications in nucleic acids, several investigators have chemically synthesized nucleosides, nucleotides and phosphoramidites with various base and sugar modifications and incorporated them into oligonucleotides.

Uhlmann and Peyman, 1990, *Chem. Reviews* 90, 543, review the use of nucleoside modifications to stabilize antisense oligonucleotides.

Usman et al., International PCT Publication Nos. WO/93/15187; and WO 95/13378; describe the use of sugar, base and backbone modifications to enhance the nuclease stability of enzymatic nucleic acid molecules.

Eckstein et al., International PCT Publication No. WO 92/07065 describe the use of sugar, base and backbone modifications to enhance the nuclease stability of enzymatic nucleic acid molecules.

Grasby et al., 1994, *Proc. Indian Acad. Sci.,* 106, 1003, review the "applications of synthetic oligoribonucleotide analogues in studies of RNA structure and function".

Eaton and Pieken, 1995, *Annu. Rev. Biochem.,* 64, 837, review sugar, base and backbone modifications that enhance the nuclease stability of RNA molecules.

Hildbrand and Leumann, 1996, *Agnew. Chem. Int. Ed. Engl.,* 35, 1968, describe a method for the synthesis of a 2-aminopyridine nucleoside derivative.

The references cited above are distinct from the presently claimed invention since they do not disclose and/or contemplate the synthesis of the nucleoside analogs of the instant invention.

SUMMARY OF THE INVENTION

This invention relates to novel nucleoside analogs having the Formula I:

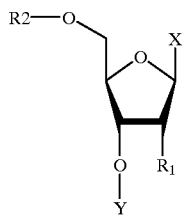

wherein, $R_1$ is independently H, OH, O—$R_3$, where $R_3$ is independently a moiety selected from a group consisting of alkyl, alkenyl, alkynyl, aryl, alkylaryl, carbocyclic aryl, heterocyclic aryl, amide and ester; C—$R_3$, where $R_3$ is independently a moiety selected from a group consisting of alkyl, alkenyl, alkynyl, aryl, alkylaryl, carbocyclic aryl, heterocyclic aryl, amide and ester; halo, $NHR_4$ ($R_4$=alkyl (C1–22), acyl (C1–22), substituted or unsubstituted aryl), or $OCH_2SCH_3$ (methylthiomethyl); X is independently a nucleotide base selected from a group consisting of 2-fluoropyridine-3-yl, pyridin-2-one-3-yl, pyridin-2-(4-nitrophenylethyl)-one-3-yl, 2-bromopyridine-5-yl, pyridin-2-one-5-yl, 2-aminopyridine-5-yl, and pyridin-2-(4-nitrophenylethyl)-one-5-yl; Y is independently a phosphorus-containing group; and R2 is independently DMT or a phosphorus-containing group.

In one preferred embodiment the invention features novel nucleoside analogs having the Formula II:

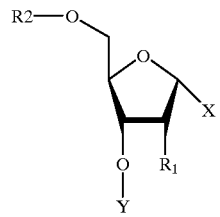

wherein, $R_1$ is independently H, OH, O—$R_3$, where $R_3$ is independently a moiety selected from a group consisting of alkyl, alkenyl, alkynyl, aryl, alkylaryl, carbocyclic aryl, heterocyclic aryl, amide and ester; C—$R_3$, where $R_3$ is independently a moiety selected from a group consisting of alkyl, alkenyl, alkynyl, aryl, alkylaryl, carbocyclic aryl, heterocyclic aryl, amide and ester; halo, $NHR_4$ ($R_4$=alkyl (C1–22), acyl (C1–22), substituted or unsubstituted aryl), or $OCH_2SCH_3$ (methylthiomethyl); X is independently a nucleotide base selected from a group consisting of 2-fluoropyridine-3-yl, 2-bromopyridine-5-yl, pyridin-2-one-5-yl, and 2-aminopyridine-5-yl; Y is independently a phosphorus-containing group; and R2 is independently DMT or a phosphorus-containing group.

Specifically, an "alkyl" group refers to a saturated aliphatic hydrocarbon, including straight-chain, branched-chain, and cyclic alkyl groups. Preferably, the alkyl group has 1 to 12 carbons. More preferably it is a lower alkyl of from 1 to 7 carbons, more preferably 1 to 4 carbons. The alkyl group may be substituted or unsubstituted. When substituted the substituted group(s) is preferably, hydroxy, cyano, alkoxy, $NO_2$ or $N(CH_3)_2$, amino, or SH.

The term "alkenyl" group refers to unsaturated hydrocarbon groups containing at least one carbon-carbon double bond, including straight-chain, branched-chain, and cyclic groups. Preferably, the alkenyl group has 1 to 12 carbons.

More preferably it is a lower alkenyl of from 1 to 7 carbons, more preferably 1 to 4 carbons. The alkenyl group may be substituted or unsubstituted. When substituted the substituted group(s) is preferably, hydroxyl, cyano, alkoxy, $NO_2$, halogen, $N(CH_3)_2$, amino, or SH.

The term "alkynyl" refers to an unsaturated hydrocarbon group containing at least one carbon-carbon triple bond, including straight-chain, branched-chain, and cyclic groups. Preferably, the alkynyl group has 1 to 12 carbons. More preferably it is a lower alkynyl of from 1 to 7 carbons, more preferably 1 to 4 carbons. The alkynyl group may be substituted or unsubstituted. When substituted the substituted group(s) is preferably, hydroxyl, cyano, alkoxy, =O, =S, $NO_2$ or $N(CH_3)_2$, amino or SH.

An "aryl" group refers to an aromatic group which has at least one ring having a conjugated π electron system and includes carbocyclic aryl, heterocyclic aryl and biaryl groups, all of which may be optionally substituted. The preferred substituent(s) on aryl groups are halogen, trihalomethyl, hydroxyl, SH, cyano, alkoxy, alkyl, alkenyl, alkynyl, and amino groups.

An "alkylaryl" group refers to an alkyl group (as described above) covalently joined to an aryl group (as described above).

"Carbocyclic aryl" groups are groups wherein the ring atoms on the aromatic ring are all carbon atoms. The carbon atoms are optionally substituted.

"Heterocyclic aryl" groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, pyrrolo, pyrimidyl, pyrazinyl, imidazolyl and the like, all optionally substituted.

An "amide" refers to an —C(O)—NH—R, where R is either alkyl, aryl, alkylaryl or hydrogen.

An "ester" refers to an —C(O)—OR', where R is either alkyl, aryl, alkylaryl or hydrogen.

A "blocking group" is a group which is able to be removed for polynucleotide synthesis and/or which is compatible with solid phase polynucleotide synthesis.

A "phosphorus containing group" can include phosphorus in forms such as dithioates, phosphoramidites and/or as part of an oligonucleotide.

In a preferred embodiment, the invention features a process for synthesis of novel nucleoside analogs of formula I or II.

In yet another preferred embodiment, the invention features the incorporation of novel nucleoside analogs of Formula I or II or combinations thereof, into polynucleotides. These novel nucleoside analogs can be incorporated into polynucleotides enzymatically. For example by using bacteriophage T7 RNA polymerase, these novel nucleoside analogs can be incorporated into RNA at one or more positions (Milligan et al., 1989, *Methods Enzymol.*, 180, 51). Alternatively, novel nucleoside analogs can be incorporated into polynucleotides using solid phase synthesis (Brown and Brown, 1991, in *Oligonucleotides and Analogues: A Practical Approach,* p. 1, ed. F. Eckstein, Oxford University Press, New York; Wincott et al., 1995, *Nucleic Acids Res.,* 23, 2677; Beaucage & Caruthers, 1996, in *Bioorganic Chemistry: Nucleic Acids,* p 36, ed. S. M. Hecht, Oxford University Press, New York).

The novel nucleoside analogs of Formula I or II or combinations thereof, can be used for chemical synthesis of nucleotides, nucleotide-tri-phosphates and/or phosphoramidites as building blocks for selective incorporation into oligonucleotides. These oligonucleotides can be used as an antisense molecule, 2-5A antisense chimera, triplex forming oligonucleotides (TFO) or as an enzymatic nucleic acid molecule. The oligonucleotides can also be used as probes or primers for synthesis and/or sequencing of RNA or DNA.

The novel nucleoside analogs of Formula I or II or combinations thereof, can also be independently or in combination used as an antiviral, anticancer or an antitumor agent. These compounds can also be independently or in combination used with other antiviral, anticancer or an antitumor agents.

By "antisense" it is meant a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review see Stein and Cheng, 1993 *Science* 261, 1004).

By "2-5A antisense chimera" it is meant, an antisense oligonucleotide containing a 5' phosphorylated 2'-5'-linked adenylate residues. These chimeras bind to target RNA in a sequence-specific manner and activate a cellular 2-5A-dependent ribonuclease which, in turn, cleaves the target RNA (Torrence et al., 1993 *Proc. Natl. Acad. Sci. USA* 90, 1300).

By "triplex forming oligonucleotides (TFO)" it is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504).

By "enzymatic nucleic acid" it is meant a nucleic acid molecule capable of catalyzing reactions including, but not limited to, site-specific cleavage and/or ligation of other nucleic acid molecules, cleavage of peptide and amide bonds, and trans-splicing.

The enzymatic nucleic acid is able to intramolecularly or intermolecularly cleave RNA or DNA and thereby inactivate a target RNA or DNA molecule. The enzymatic nucleic acid molecule that has complementarity in a substrate binding region to a specified gene target, also has an enzymatic activity that specifically cleaves RNA or DNA in that target. This complementarity functions to allow sufficient hybridization of the enzymatic RNA molecule to the target RNA or DNA to allow the cleavage to occur. 100% Complementarity is preferred, but complementarity as low as 50–75% may also be useful in this invention. The nucleic acids may be modified at the base, sugar, and/or phosphate groups.

The term enzymatic nucleic acid is used interchangeably with phrases such as ribozymes, catalytic RNA, enzymatic RNA, catalytic DNA, nucleozyme, DNAzyme, RNA enzyme, endoribonuclease, minizyme, leadzyme or DNA enzyme. All of these terminologies describe nucleic acid molecules with enzymatic activity.

By "complementarity" is meant a nucleic acid that can form hydrogen bond(s) with other RNA sequence by either traditional Watson-Crick or other non-traditional types (for example, Hoogsteen type) of base-paired interactions.

Nucleic acid molecules having an endonuclease enzymatic activity are able to repeatedly cleave other separate RNA molecules in a nucleotide base sequence-specific manner. Such enzymatic RNA molecules can be targeted to virtually any RNA transcript, and efficient cleavage achieved in vitro (Zaug et al., 324, *Nature* 429 1986; Kim et al., 84 *Proc. Natl. Acad. Sci. USA* 8788, 1987; Haseloff and Gerlach, 334 *Nature* 585, 1988; Cech, 260 *JAMA* 3030, 1988; and Jefferies et al., 17 *Nucleic Acids Research* 1371, 1989).

Because of their sequence-specificity, trans-cleaving ribozymes show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Ribozymes can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

Seven basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the effective concentration of ribozyme necessary to effect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base-pairing. Thus, it is thought that the specificity of action of a ribozyme is greater than that of antisense oligonucleotide binding the same RNA site.

In one of the preferred embodiments of the inventions herein, the enzymatic nucleic acid molecule is formed in a hammerhead or hairpin motif, but may also be formed in the motif of a hepatitis δ virus, group I intron, group II intron or RNaseP RNA (in association with an RNA guide sequence) or Neurospora VS RNA. Examples of such hammerhead motifs are described by Dreyfus, supra, Rossi et al., 1992, *AIDS Research and Human Retroviruses* 8, 183; of hairpin motifs by Hampel et al., EP0360257, Hampel and Tritz, 1989 *Biochemistry* 28, 4929, Feldstein et al., 1989, *Gene* 82, 53, Haseloff and Gerlach, 1989, *Gene,* 82, 43, and Hampel et al., 1990 *Nucleic Acids Res.* 18, 299; of the hepatitis δ virus motif is described by Perrotta and Been, 1992 *Biochemistry* 31, 16; of the RNaseP motif by Guerrier-Takada et al., 1983 *Cell* 35, 849; Forster and Altman, 1990, *Science* 249, 783; Li and Altman, 1996, *Nucleic Acids Res.* 24, 835; Neurospora VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799; Guo and Collins, 1995, *EMBO. J.* 14, 363); Group II introns are described by Griffin et al., 1995, *Chem. Biol.* 2, 761; Michels and Pyle, 1995, *Biochemistry* 34, 2965; Pyle et al., International PCT Publication No. WO 96/22689; and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

Synthesis of nucleic acids greater than 100 nucleotides in length is difficult using automated methods, and the therapeutic cost of such molecules is prohibitive. In this invention, small nucleic acid motifs (e.g., antisense oligonucleotides, hammerhead or the hairpin ribozymes) are used for exogenous delivery. The simple structure of these molecules increases the ability of the nucleic acid to invade targeted regions of the mRNA structure.

The novel nucleoside analogs of the instant invention and/or the polynucleotides comprising these analogs are added directly to a cell, or can be complexed with cationic lipids, packaged within liposomes, or otherwise delivered to target cells. The nucleosides, nucleic acid or nucleic acid complexes can be locally administered to relevant tissues ex vivo, or in vivo through injection, infusion pump or stent, with or without their incorporation in biopolymers.

By "enzymatic portion" is meant that part of the ribozyme essential for cleavage of an RNA substrate.

By "substrate binding arm" is meant that portion of a ribozyme which is complementary to (i.e., able to base-pair with) a portion of its substrate. Generally, such complementarity is 100%, but can be less if desired. For example, as few as 10 bases out of 14 may be base-paired. Such arms are shown generally in FIGS. 1–3 as discussed below. That is, these arms contain sequences within a ribozyme which are intended to bring ribozyme and target RNA together through complementary base-pairing interactions; e.g., ribozyme sequences within stems I and III of a standard hammerhead ribozyme make up the substrate-binding domain (see FIG. 1).

By "unmodified nucleoside" is meant one of the bases adenine, cytosine, guanosine, uracil joined to the 1' carbon of β-D-ribo-furanose.

By "modified nucleoside" is meant any nucleotide base which contains a modification in the chemical structure of an unmodified nucleotide base.

Other features and advantages of the invention will be apparent from the following description of the preferred embodiments thereof, and from the claims.

DESCRIPTION OF THE PREFERRED EMBODIMENTS

The drawings will first briefly be described.
Drawings
FIG. 1 is a diagrammatic representation of the hammerhead ribozyme domain known in the art. Stem II can be $\geq 2$ base-pair long. Each N is independently any base or non-nucleotide as used herein.

FIG. 2a is a diagrammatic representation of the hammerhead ribozyme domain known in the art; FIG. 2b is a diagrammatic representation of the hammerhead ribozyme as divided by Uhlenbeck (1987, *Nature,* 327, 596–600) into a substrate and enzyme portion; FIG. 2c is a similar diagram showing the hammerhead divided by Haseloff and Gerlach (1988, *Nature,* 334, 585–591) into two portions; and FIG. 2d is a similar diagram showing the hammerhead divided by Jeffries and Symons (1989, *Nucl. Acids. Res.,* 17, 1371–1371) into two portions.

FIG. 3 is a diagrammatic representation of the general structure of a hairpin ribozyme. Helix 2 (H2) is provided with at least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq$1 base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq$2 bases. The connecting loop can also be replaced with a non-nucleotide linker molecule. H, refers to bases A, U or C. Y refers to pyrimidine bases." - - - " refers to a chemical bond.

Figure 6:
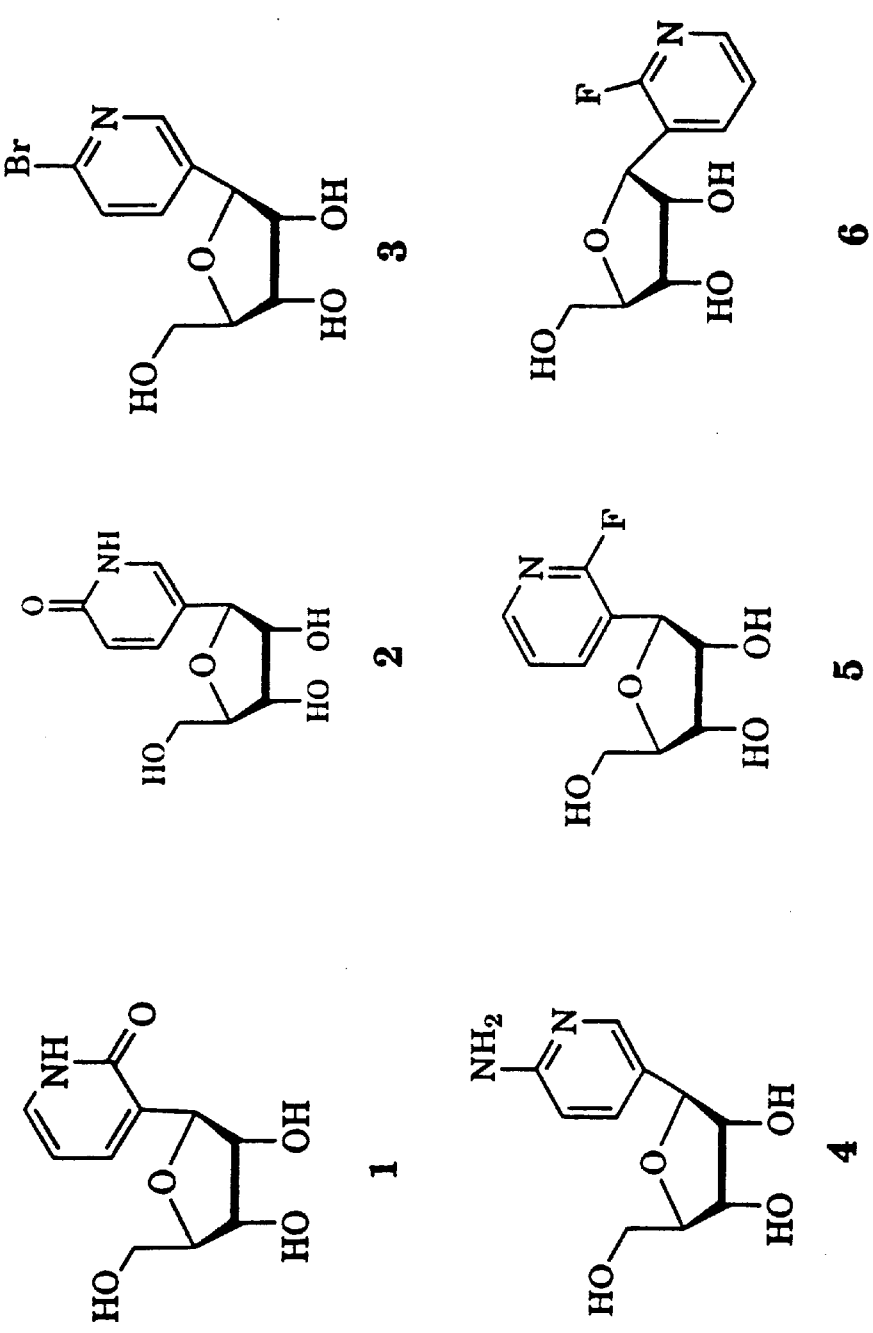
FIG. 6 is a diagrammatic representation of a few of the novel nucleoside analogs of the instant invention. 1, 3-($\beta$-D-Ribofuranosyl)-pyridin-2-one; 2, 5-($\beta$-D-Ribofuranosyl)-pyridin-2-one; 3, 5-($\beta$-D-Ribofuranosyl)-2-bromopyridine; 4, 5-($\beta$-D-Ribofuranosyl)-2-aminopyridine; 5, 3-($\beta$-D-Ribofuranosyl)-2-fluoropyridine; 6, 3-($\alpha$-D-Ribofuranosyl)-2-fluoropyridine.

FIG. 8 describes two schemes for the synthesis of 3-($\beta$-D-Ribofuranosyl)-pyridin-2-one (1 in FIG. 6 and 13 in FIG. 8B) and 3-($\beta$-D-Ribofuranosyl)-2-fluoropyridine (5 in FIG. 6 and 12 in FIG. 8B) monomers.

FIG. 9 is a scheme for the synthesis of 1-(5-O-Dimethoxytrityl-2-O-tert-butyldimethylsilyl-3-O-2-cyanoethyl-N,N-diisopropylaminophosphoramidite-$\beta$-D-ribofuranosyl)-1,4-dihydro-pyrimidine-4-one.

FIG. 10 is a scheme for the synthesis of 1-(5-O-Dimethoxytrityl-2-O-tert-butyidimethylsilyl-3-O-2-cyanoethyl-N, N-diisopropylaminophosphoramidite-$\beta$-D-Ribofuranosyl)-1,4-dihydro-pyrimidine-2-one.

FIG. 11 is a scheme for the synthesis of 5'-O-Dimethoxytrityl-2'-O-tert-Butyidimethylsilyl-O$^4$-Diphenylcarbamoyl-3-Deaza Uridine 3'-(2-Cyanoethyl N,N-diisopropylphosphoramidite).

FIG. 12 is a scheme for the synthesis of 5'-O-dimethoxytrityl-2'-O-tert-butyidimethylsilyl-O$^4$-diphenylcarbamoyl-3-deaza cytidine 3'-(2-Cyanoethyl N,N-diisopropylphosphoramidite).

FIG. 13 is a scheme for the synthesis of 2-O-t-Butyldimethylsilyl-5-O-Dimethoxytrityl-3-O-(2-Cyanoethyl-N,N-diisopropylphosphoramidite)-$\beta$-D-ribofuranosylindole.

FIG. 14 is a scheme for the synthesis of 2-O-t-Butyidimethylsilyl-5-O-Dimethoxytrityl-3-O-(2-Cyanoethyl-N,N-diisopropylphosphoramidite)-$\beta$-D-ribofuranosylbenzimidazole.

FIG. 15 is a scheme for the synthesis of 3-($\beta$-D-Ribofuranosyl)-Pyridine-2-(4-Nitrophenylethyl)-One and 5-($\beta$-D-Ribofuranosyl)-Pyridine-2-(4-Nitrophenylethyl)-One Phosphoramidite.

SYNTHESIS OF POLYNUCLEOTIDES

Synthesis of polynucleotides greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure.

RNA molecules, such as the ribozymes are chemically synthesized. The method of synthesis used follows the procedure for normal RNA synthesis as described in Usman et al., 1987 *J Am. Chem. Soc.,* 109, 7845; Scaringe et al., 1990 *Nucleic Acids Res.,* 18, 5433; and Wincott et al., 1995 *Nucleic Acids Res.* 23, 2677–2684 and makes use of common nucleic acid protecting and coupling groups, such as dimethoxytrityl at the 5'-end, and phosphoramidites at the 3'-end. Small scale synthesis were conducted on a 394 Applied Biosystems, Inc. synthesizer using a modified 2.5 mol scale protocol with a 5 min coupling step for alkylsilyl protected nucleotides and 2.5 min coupling step for 2'-O-methylated nucleotides. Table 2 outlines the amounts, and the contact times, of the reagents used in the synthesis cycle. A 6.5-fold excess (163 $\mu$L of 0.1 M =16.3 $\mu$mol) of phosphoramidite and a 24-fold excess of S-ethyl tetrazole (238 $\mu$L of 0.25 M=59.5 $\mu$mol) relative to polymer-bound 5'-hydroxyl was used in each coupling cycle. Average coupling yields on the 394 Applied Biosystems, Inc. synthesizer, determined by calorimetric quantitation of the trityl fractions, were 97.5–99%. Other oligonucleotide synthesis reagents for the 394 Applied Biosystems, Inc. synthesizer: detritylation solution was 2% TCA in methylene chloride (ABI); capping was performed with 16% N-methyl imidazole in THF (ABI) and 10% acetic anhydride/10% 2,6-lutidine in THF (ABI); oxidation solution was 16.9 mM I$_2$, 49 mM pyridine, 9% water in THF (Millipore). B & J Synthesis Grade acetonitrile was used directly from the reagent bottle. S-Ethyl tetrazole solution (0.25 M in acetonitrile) was made up from the solid obtained from American International Chemical, Inc.

Deprotection of the RNA was performed as follows. The polymer-bound oligoribonucleotide, trityl-off, was transferred from the synthesis column to a 4 mL glass screw top vial and suspended in a solution of methylamine (MA) at 65° C. for 10 min. After cooling to −20° C., the supernatant was removed from the polymer support. The support was washed three times with 1.0 mL of EtOH:MeCN:H$_2$O/3:1:1, vortexed and the supernatant was then added to the first supernatant. The combined supernatants, containing the oligoribonucleotide, were dried to a white powder.

The base-deprotected oligoribonucleotide was resuspended in anhydrous TEA-HF/NMP solution (250 $\mu$L of a solution of 1.5 mL N-methylpyrrolidinone, 750 µL TEA and 1.0 mL TEA.3HF to provide a 1.4M HF concentration) and heated to 65° C. for 1.5 h. The resulting, fully deprotected, oligomer was quenched with 50 mM TEAB (9 mL) prior to anion exchange desalting.

For anion exchange desalting of the deprotected oligomer, the TEAB solution was loaded onto a Qiagen 500® anion exchange cartridge (Qiagen Inc.) that was prewashed with 50 mM TEAB (10 mL). After washing the loaded cartridge with 50 mM TEAB (10 mL), the RNA was eluted with 2 M TEAB (10 mL) and dried down to a white powder.

Inactive hammerhead ribozymes were synthesized by substituting a U for $G_5$ and a U for $A_{14}$ (numbering from (Hertel, K. J., et al., 1992, Nucleic Acids Res., 20, 3252)).

The average stepwise coupling yields were >98% (Wincott et al., 1995 Nucleic Acids Res. 23, 2677–2684).

Hairpin ribozymes are synthesized either as one part or in two parts and annealed to reconstruct the active ribozyme (Chowrira and Burke, 1992 Nucleic Acids Res., 20, 2835–2840).

RNAs are purified by gel electrophoresis using general methods or are purified by high pressure liquid chromatography (HPLC; See Stinchcomb et al., International PCT Publication No. WO 95/23225, the totality of which is hereby incorporated herein by reference) and are resuspended in water.

Various modifications to ribozyme structure can be made to enhance the utility of ribozymes. Such modifications will enhance shelf-life, half-life in vitro, stability, and ease of introduction of such ribozymes to the target site, eg., to enhance penetration of cellular membranes, and confer the ability to recognize and bind to targeted cells.

Optimizing Ribozyme Activity

Figure 1:
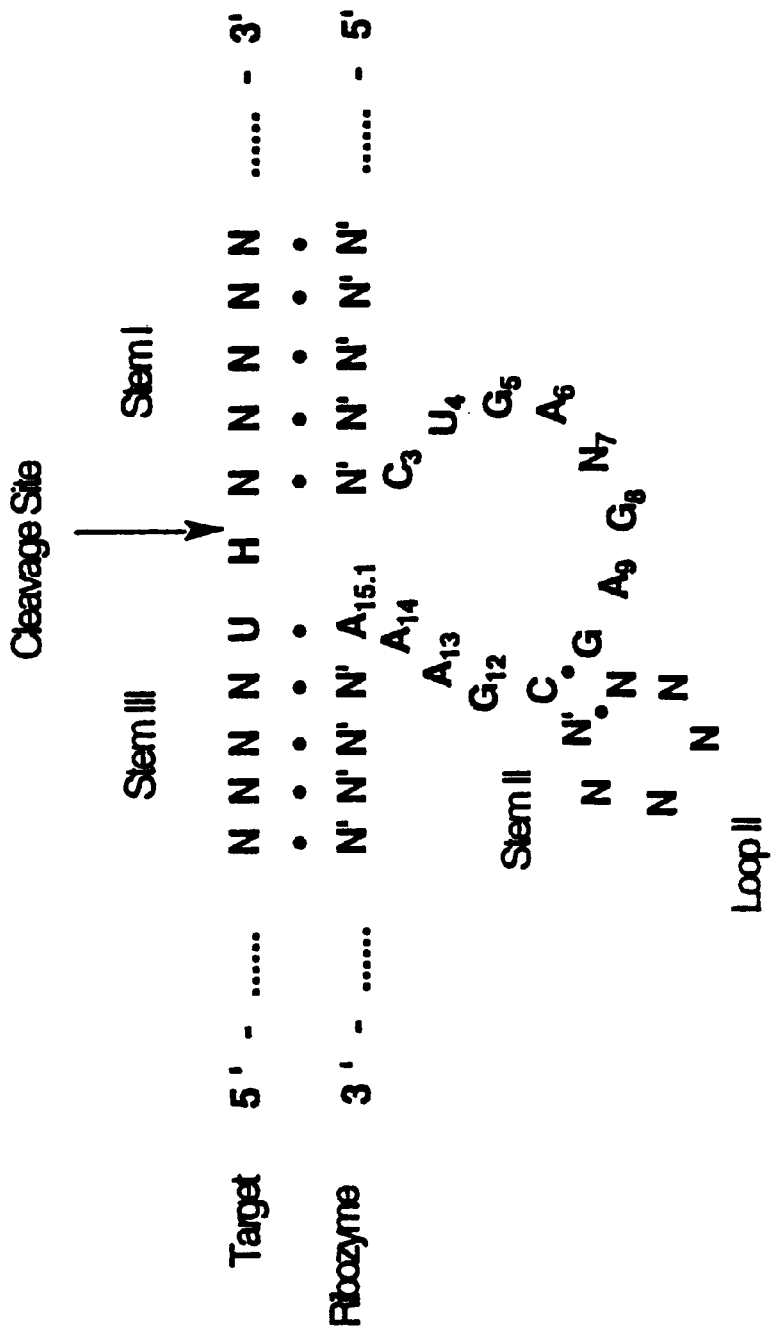
Figure 2:
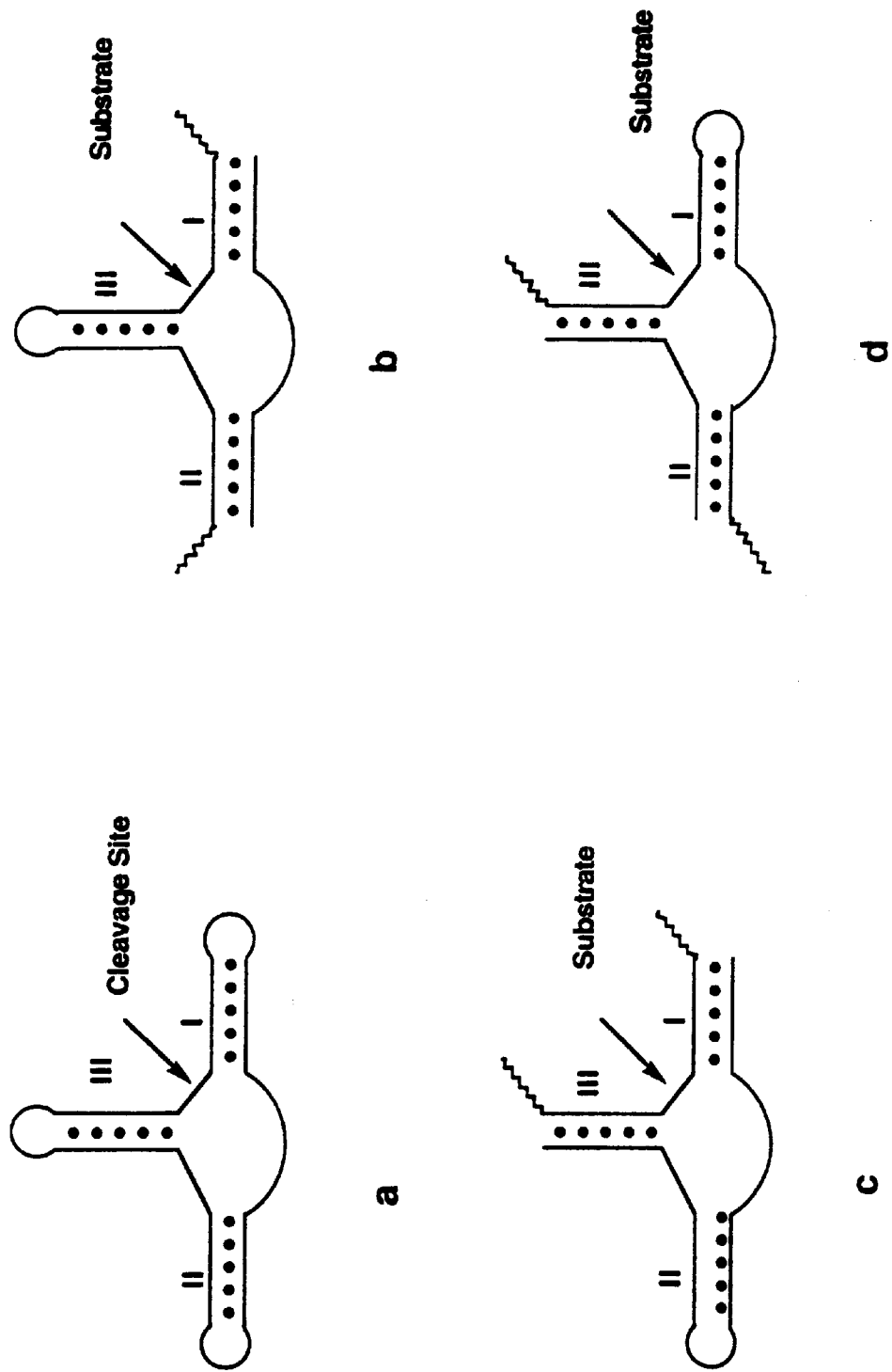
Figure 3:
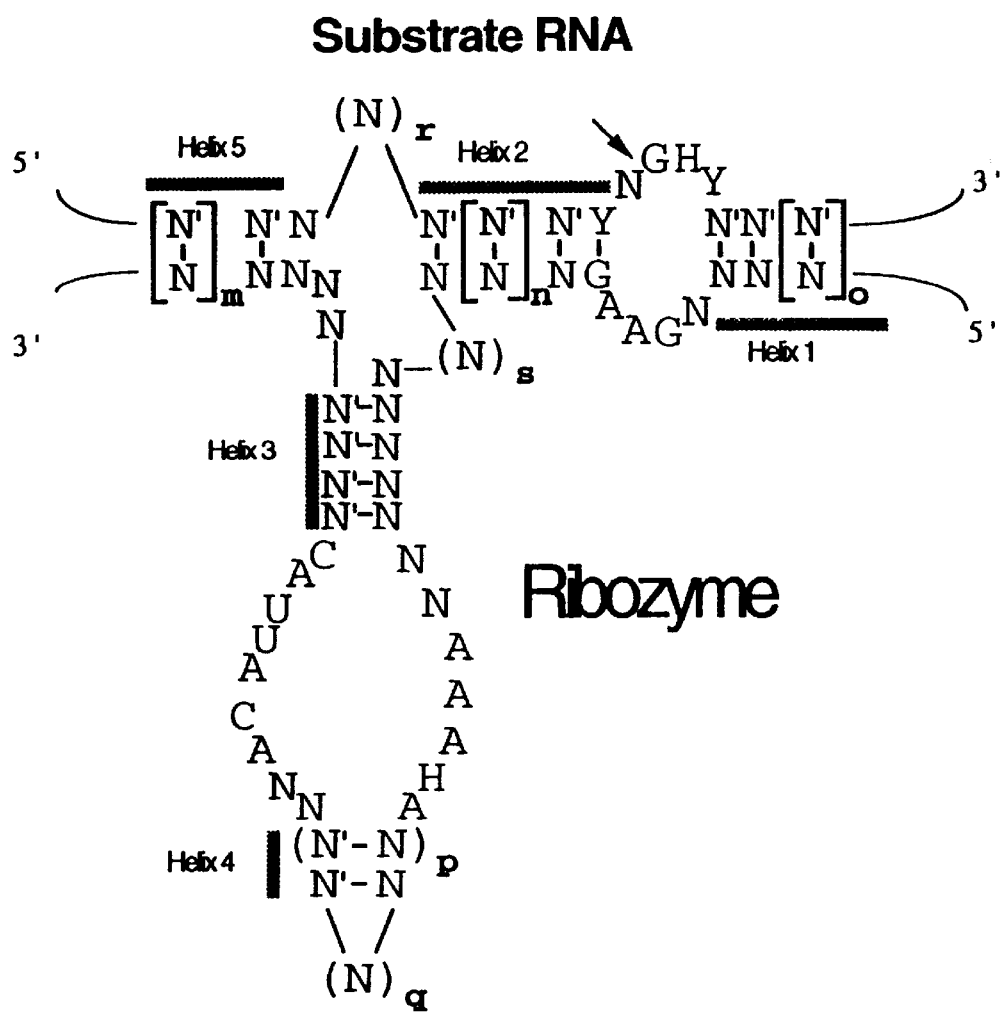
Figure 4:
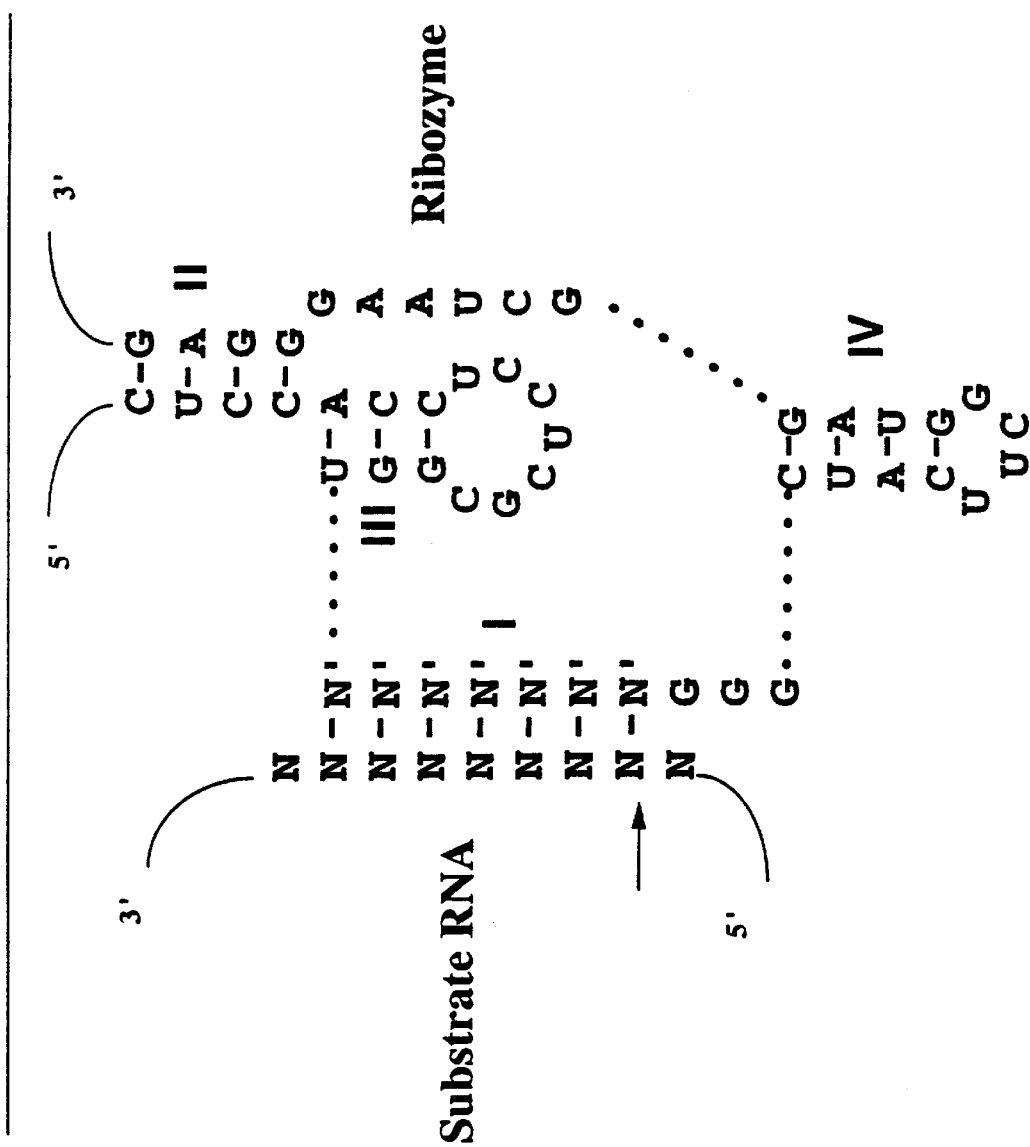
FIG. 4 is a representation of the general structure of the hepatitis delta virus ribozyme domain known in the art. Each N is independently any base or non-nucleotide as used herein.
Figure 5:
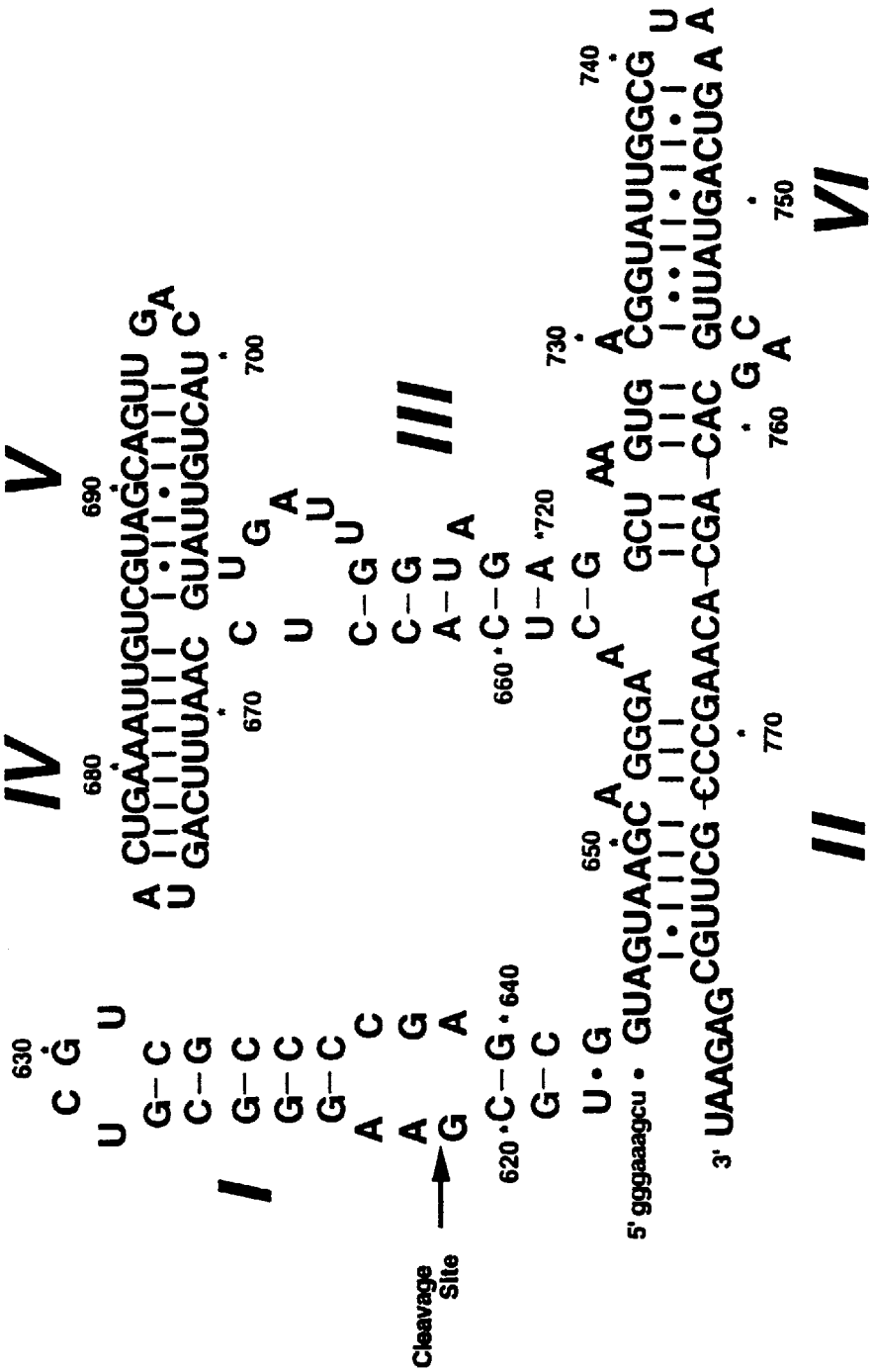
FIG. 5 is a representation of the general structure of the self-cleaving VS RNA ribozyme domain.

Ribozyme activity can be optimized as described by Stinchcomb et al., supra. The details will not be repeated here, but include altering the length of the ribozyme binding arms (stems I and II, see FIG. 2c), or chemically synthesizing ribozymes with modifications that prevent their degradation by serum ribonucleases (see e.g., Eckstein et al., International Publication No. WO 92/07065; Perrault et al., 1990 Nature 344, 565; Pieken et al., 1991 Science 253, 314; Usman and Cedergren, 1992 Trends in Biochem. Sci. 17, 334; Usman et al., International Publication No. WO 93/15187; Rossi et al., International Publication No. WO 91/03162; as well as Sproat, U.S. Pat. No. 5,334,711 which describe various chemical modifications that can be made to the sugar moieties of enzymatic RNA molecules). Modifications which enhance their efficacy in cells, and removal of stem II bases to shorten RNA synthesis times and reduce chemical requirements are desired. (All these publications are hereby incorporated by reference herein).

Administration of Ribozyme

Sullivan et al., PCT WO 94/02595, describes the general methods for delivery of enzymatic RNA molecules . Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., PCT WO93/23569 which have been incorporated by reference herein.

EXAMPLES

The following are non-limiting examples showing the synthesis and activity of base-modified catalytic nucleic acids. Those in the art will recognize that certain reaction conditions such as temperatures, pH, ionic conditions, reaction times and solvent conditions described in the following examples are not meant to be limiting and can be readily modified without significantly effecting the synthesis.

Example 1

Synthesis of Ribozymes Containing Base-Modified Nucleotides

The method of synthesis used follows the procedure for normal RNA synthesis as described in Usman et al., J. Am. Chem. Soc. 1987, 109, 7845–7854; Scaringe et al., Nucleic Acids Res. 1990, 18, 5433–5441 and Wincott et al., 1995 Nucleic Acids Res. 23, 2677–2684 and makes use of common nucleic acid protecting and coupling groups, such as dimethoxytrityl at the 5'-end, and phosphoramidites at the 3'-end (compounds 4, 9, 13, 17, 22, 23). The average stepwise coupling yields were >98%. These base-modified nucleotides may be incorporated not only into hammerhead ribozymes, but also into hairpin, VS ribozymes, hepatitis delta virus, or Group I or Group II introns. They are, therefore, of general use as replacement motifs in any nucleic acid structure.

Example 2

Synthesis of 5-(β-D-Ribofuranosyl)-Pyridin-2-one (2)

Figure 7:
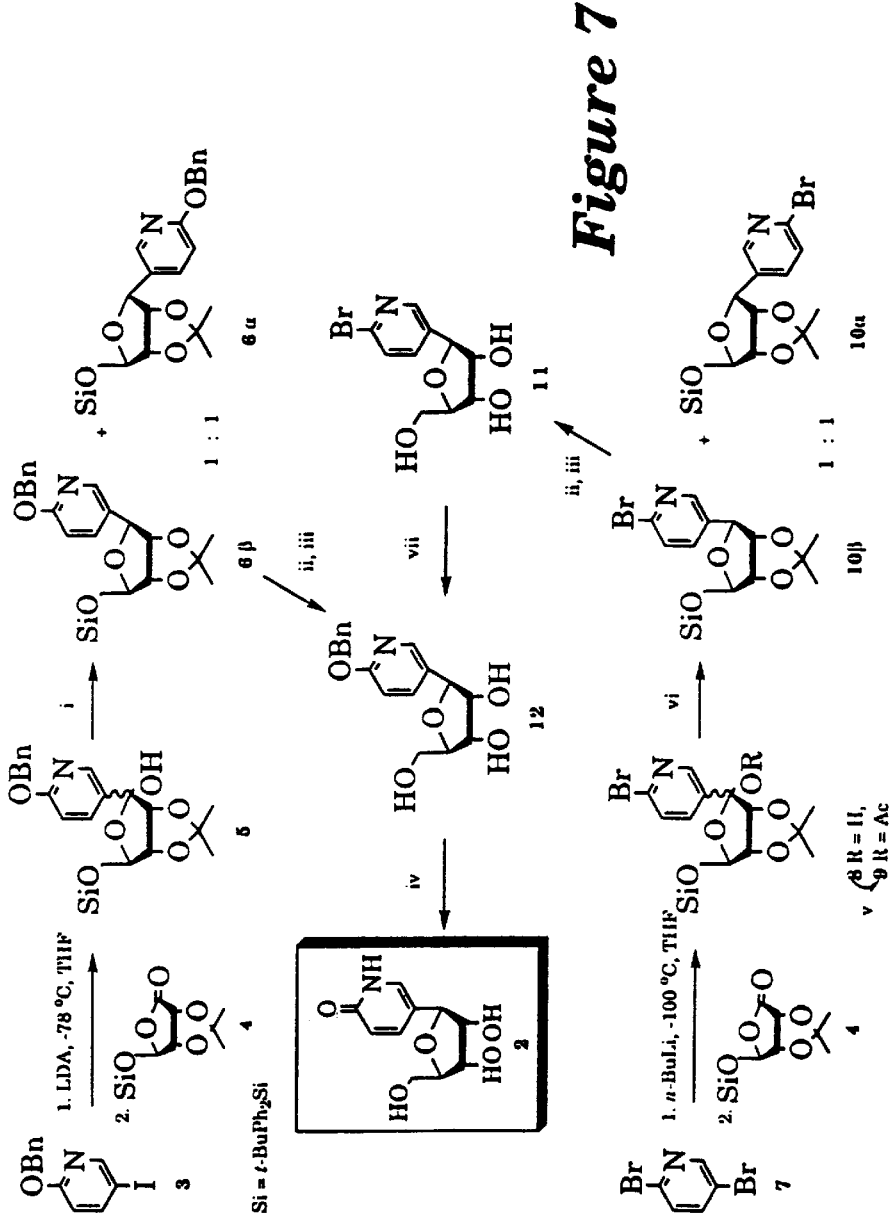
FIG. 7 is a scheme for the synthesis of 5-($\beta$-D-Ribofuranosyl)-pyridin-2-one (2 in FIG. 6) and 5-($\beta$-D-Ribofuranosyl)-2-bromopyridine (3 in FIG. 6 and 11 in FIG. 7) monomers.

Referring to FIG. 7, Pyridin-2-one C-nucleoside 2 (FIG. 6) was prepared in 5 steps from 2-(benzyloxy)-5-iodopyridine (3) and D-ribono-1,4-lactone 4 and alternatively, in 7 steps from 2,5-dibromopyridine (7) and D-ribono-1,4-lactone 4 . The intermediate 1'-O-Ac derivative 9 was crucial for the successful deoxygenation of hemiacetal 8.

The synthesis of a pyrimidine nucleoside analog 2 which lacks $O^2$ carbonyl is described herein. These analogs of pyrimidine nucleosides with novel H-bonding patterns could serve as valuable tools for identification of essential intramolecular hydrogen bonding interactions. 2'-Deoxy analog of 1 (Solomon, M. S.; Hopkins, P. B. Tetrahedron Lett. 1991, 32, 3297–3300; Solomon, M. S.; Hopkins, P. B. J. Org. Chem. 1993, 58, 2232–2243) and 1 is described as a mixture of α and β anomers (Belmas et al., 1989 Nucleosides & Nucleotides 8, 307). The ribo derivative 2 is not known and are described here.

In one attempt to synthesize 2 (FIG. 7) Applicant converted 2-(benzyloxy)-5-iodopyridine (3) (synthesized from 2-bromo-5-iodopyridine (Hama et al., Bull. Chem. Soc. Jpn. 1988, 61, 1683–1686) using reducing reagents such as NaH/BnOH/DMF) to 5-lithio derivative by metallation using reagents such as, lithium diazapropylamine (LDA) under suitable conditions such as using a temperature of about −78° C. Condensation of a protected D-ribonolactone, such as 5-O-t-butyldiphenylsilyl-2,3-O-isopropylidene-D- ribonolactone (4) with this intermediate (5-lithio derivative) yielded the mixture of α and β lactols 5 in 1:8 ratio (47% yield). It should be noted that for hemiacetals 5, 8 and 9, the prefix ax refers to the position of the glycosidic OH group relative to the configuration at the reference C-atom (C4' in 2; i.e. the pyridyl moiety is in the β-position). The assignments of the anomeric configurations were based on $\Delta\delta$ values for the isopropylidene Me groups in $^1$H NMR spectra. It is known from the previous work (Gudmundsson et al., *Tetrahedron Lett.* 1996, 37, 2365–2368; Dondoni, A.; Scherrmann, M.-C. *J. Org. Chem.* 1994, 59, 6404–6412) that reductive 1'-deacetoxylation is a much more efficient approach to 1'-deoxygenation than direct reduction of 1'-OH. Unfortunately, acetylation of 5 with $Ac_2O$/DMAP/ TEA in acetonitrile failed; the major product did not contain acetyl group by $^1$H NMR.

Reduction of 5 with reducing agents, such as triethylsilane $(Et_3SiH)/BF_3.Et_2O$ in acetonitrile at temperatures such as room temperature yielded an 1:1 α/β mixture of C-nucleosides 6 in 21% yield. 6β and 6α were easily separated by flash column chromatography using 5–10% gradient of methanol in dichloromethane for elution.

6β was deblocked using reagents such as TBAF to remove the 5'-silyl ether protection followed by the cleavage of isopropylidene group with acid to yield 12 in a good yield ($^1$H NMR $(CD_3)_2CO+D_2O$) data for 12: δ8.19 (d, $J_{6,4}$=2.4, 1H, H6), 7.79 (dd,$J_{4,3}$=8.4, $J_{4,6}$=2.4, 1H, H4), 6.80 (d, $J_{3,4}$=8.4, 1H, H3), 5.37 (s, 2H, $CH_2Ph$), 4.64 (d, $J_{1',2'}$=7.2, 1H, H1'), 4.12 (dd,$J_{3',2'}$=5.4, $J_{3',4'}$=3.4, 1H, H3'), 3.95 (m, 1H, H4'), 3.88 (dd, $J_{2',1'}$=7.2, $J_{2',3'}$=5.4, 1H, H2'), 3.74 (dd, $J_{5',4'}$=3.6, $J_{5',5''}$=12.0, 1H, H5'), 3.69 (dd, $J_{5'',4'}$=4.2, $J_{5'',5'}$=12.0, 1H, H5").

Compound 12 was obtained by removing the Bzl group using a variety of different approaches, such as cleavage of benzyl ether group of 12 using trimethylsilyl iodide (TMSI) in dichloromethane yielding the free C-nucleoside 2 in a good yield.

Parham and Piccirilli (*J. Org. Chem.* 1977, 42, 257–260) described an unexpected and highly selective halogen-lithium exchange between 2,5-dibromopyridine (7) and n-butyllithium at very low temperature (–100° C.), where only 5-bromo substituent was exchanged. Applicant synthesized 2 by an alternative approach starting from 7 and D-ribono-1,4-lactone 4 (Scheme 1). Metallation of 7 at about –100° C. in THF and condensation of the resulting lithiated pyridine with protected D-ribono-1,4-lactone 4 at –100° C. afforded the expected hemiacetal 8 (44% yield, α/β 1:12) along with two by-products in 6% and 17% yield, respectively.

Procedure for the preparation of 8: 2,5-dibromopyridine 7 (1.75 g, 7.4 mmol) was dissolved in dry THF (46 ml) under argon and the solution was cooled to –100° C. 1.6 M n-BuLi in hexanes (5.09 ml, 8.14 mmol) was added dropwise over 5 min and the solution stirred at –100° C. for 30 min. The solution of D-ribono-1,4-lactone 4 (3 g, 7 mmol) in dry THF (10 ml) was added dropwise over 5 min and the mixture warmed up to rt over 40 min. It was stirred additional 20 min at rt, than quenched with saturated aq. $NH_4Cl$. The mixture was extracted with ether, organic layer washed with brine, dried and evaporated to a syrup. Flash column chromatography using 3–15% gradient of ethyl acetate in hexanes eluted first 8 (1.8 g, 44%), followed by the slower product (0.23 g, 6%). At the end the slowest material eluted (0.7 g, 17%).

All three products exhibited sugar $^1$H NMR signals consistent with the hemiacetal structure. This result demonstrates the selectivity in lithiation of 7, but the formation of other products suggests that competing halogen-lithium exchange occurred, too. Deoxygenation of 8 using the same procedure as for reduction of 5 yielded, similarly as in the case of 5, an 1:1 mixture of α/β nucleosides in a low yield. On the other hand, acetylation of 8 proceeded in a quantitative yield to give 9 (only β-anomer was obtained). Reduction of 9 using $Et_3SiH/BF_3.Et_2O/CH_2Cl_2$ at 0° C.-rt proceeded in 82% yield but again without selectivity (10α/10β 1:1). The anomeric assignments were based on, besides $\Delta\delta$ of methyl groups, on the well known upfield shift of the 1'-H signal for the β-anomer compared to the α-anomer (Tam et al., *J. Org. Chem.* 1979, 44, 4854–4862; Sokolova et al., *Carbohydr. Res.* 1981, 93, 19–34). 10β was deprotected to 11 in two steps (1 M TBAF, followed by refluxing 80% acetic acid). Derivative 11 was highly resistant to displacement of 2-bromo substituent with methoxide and benzylate; only KH/BnOH/DMF at 140° C. afforded 12 in a good yield, identical in every aspect with the compound synthesized from 2-(benzyloxy)-5-iodopyridine 3. This comparison proved unequivocally that 5-pyridyl regioisomer 8 was the main product obtained from 2,5-dibromopyridine 7.

Synthesis of 5-(α-D-Ribofuranosyl)-pyridin-2-one: Treatment of 6α with TBAF to remove the 5'-silyl ether protection followed by the cleavage of isopropylidene group with acid followed by cleavage of benzyl ether group using trimethylsilyl iodide (TMSI) in dichloromethane will yield 5-(α-D-Ribofuranosyl)-pyridin-2-one in a good yield.

Synthesis of 5-(α-D-Ribofuranosyl)-2-bromopyridine: Treatment of 10α with TBAF to remove the 5'-silyl ether protection followed by the cleavage of isopropylidene group with acid will yield 5-(α-D-Ribofuranosyl)-2-bromopyridine in good yield.

Synthesis of 5-(β-D-Ribofuranosyl)-2-aminopyridine: 2-Bromo derivative 11 (580 mg, 2 mmol) was placed in a steel autoclave and the autoclave purged with a continuous stream of Ar. CuI (720 mg, 2 eq.) was added and the autoclave cooled in a Dewar vessel ($CO_2$-isopropanol). Purging over the apparatus with Ar was continued while $NH_3$ was condensed in the autoclave (ca. 15 ml). The autoclave was then quickly closed, the mixture allowed to warm to rt, placed in a heated oil bath at 115° C. and stirred for 24 h. The autoclave was then cooled as before, opened, warmed up to rt and $NH_3$ evaporated. Then, the dark mixture was dissolved in MeOH, filtered and evaporated to a syrup. Column chromatography (silica gel, MeOH/$CHCl_3$) yielded 5-(β-D-Ribofuranosyl)-2-aminopyridine (4 in FIG. 6) (235 mg, 52%).

Synthesis of 5-(α-D-Ribofuranosyl)-2-aminopyridine: 5-(α-D-Ribofuranosyl)-2-bromopyridine (580 mg, 2 mmol) was placed in a steel autoclave and the autoclave purged with a continuous stream of Ar. CuI (720 mg, 2 eq.) was added and the autoclave cooled in a Dewar vessel ($CO_2$-isopropanol). Purging over the apparatus with Ar was continued while $NH_3$ was condensed in the autoclave (ca. 15 ml). The autoclave was then quickly closed, the mixture allowed to warm to rt, placed in a heated oil bath at 115° C. and stirred for 24 h. The autoclave was then cooled as before, opened, warmed up to rt and $NH_3$ evaporated. Then, the dark mixture was dissolved in MeOH, filtered and evaporated to a syrup. Column chromatography (silica gel, MeOH/$CHCl_3$) yielded 5-(α-D-Ribofuranosyl)-2-aminopyridine.

Although the two approaches reported herein produced α/β anomers in 1:1 ratio, they represent useful methods for the preparation of larger quantities of C-nucleoside 2 for the synthesis of oligonucleotide building blocks. Both 2 and 11 might display, like other C-nucleosides, pharmaceutically useful biological activities.

Example 3

Synthesis of 3-(β-D-Ribofuranosyl)-2-Fluoropyridine (1) and 3-(β-D-Ribofuranosyl)-Pyridin-2-one (5)

Referring to FIG. 8, Pyridin-2-one C-nucleoside 13 (1 in FIG. 6) was synthesized by reducing 3 at room temperature followed by a cyclization reaction to yield compounds 5 and 8. Deblocking followed by hydrogenolysis and debenzylation yields compound 13.

Pyridin-2-one C-nucleoside 13 (1 in FIG. 6) was prepared in 7 steps from 2-fluoro-3-lithiopyridine (1) and D-ribono-1,4-lactone 2. The successful approach to β-ribofuranosides 12 (5 in FIG. 6) and 13 consisted in the reductive opening of furanose ring of hemiacetal 3 followed by intramolecular Mitsunobu cyclization.

The synthesis of a pyrimidine nucleoside analogs 12 and 13 which lack $O^4$ carbonyl is described herein and can be used for identification of essential intramolecular hydrogen bonding interactions.

The synthesis of 13 as an anomeric mixture is described from 2,4:3,5-di-O-benzylidene-aldehydo-D-ribose and 3-lithio-2-fluoropyridine (Belmans et al., *Nucleosides & Nucleotides* 1989, 8, 307–315). This procedure, however, was inefficient and not amenable to large-scale preparations due to involvement of a ribose dithioacetal during preparation of the key starting material. Besides, 2-fluropyridine derivative 12 could not be isolated by this route because of the solvolytic displacement of fluorine atom during the acid catalyzed cyclization of open chain precursor.

Referring to FIG. 8A, Applicant used a protected D-ribonolactone such as 5-O-t-butyldiphenylsilyl-2,3-O-isopropylidene-D-ribonolactone (2) in the condensation with 3-lithio-2-fluoropyridine (−78° C., than rt, 18 h, THF) and obtained 1:5 α/β mixture of lactols 3 in 63% yield (Scheme 1). It should be noted that for hemiacetals 3, the prefix a refers to the position of the glycosidic OH group relative to the configuration at the reference C-atom (C4' in 2; i.e. the pyridyl moiety is in the β-position). The assignments of the anomeric configurations were based on Δδ values for the isopropylidene Me groups in $^1$H NMR spectra. All attempts to dehydroxylate 3 using triethylsilane (Et$_3$SiH) in the presence of BF$_3$.Et$_2$O or TMSOTf in a variety of solvents resulted in poor yields of nucleosides 5. Besides, the desired β-nucleoside was always the minor anomer in the mixture. The anomeric assignments were based on, besides Δδ of isopropylidene methyl groups, on the well known upfield shift of the 1'-H signal for the β-anomer compared to the α-anomer.

It was demonstrated that the more efficient and/or selective reduction of 1'-hydroxyl group can be achieved through intermediate 1'-OAc derivative (i.e. 4; Gudmundsson et al., *Tetrahedron Lett.* 1996, 37, 2365; Dondoni et al., *J. Org. Chem.* 1994, 59, 6404–6412). Applicant found that 3 could be acetylated in a quantitative yield using Ac$_2$O/TEA/DMAP in acetonitrile to give 4 (only one isomer was generated, no attempt was made to determine its configuration). Reductive deacetoxylation of 4 with Et$_3$SiH/TMSOTf in dichloromethane at 0° C.-rt proceeded efficiently and afforded a good yield of 5 (α/β 10:1); when Et$_3$SiH was a solvent the α/β ratio was 5:1. These results are surprising because under similar reaction conditions the exclusive β-selectivity in the reduction of pyrazine (Liu et al., *Tetrahedron Lett.* 1996, 37, 5325–5328) and imidazo[1,2-a]pyridine lactols (Gudmundsson et al., *Tetrahedron Lett.* 1996, 37, 2365–2368) was reported.

In order to obtain practical quantities of β C-nucleoside Applicant investigated further several different pathways: Mesylation of 3 afforded 1'-O-mesyl derivative 6 in a moderate yield (Scheme 2). Treatment of 6 with LAH did not reduce the sulfonate as reported for 2-pyridine C-nucleosides. The more reactive LiEt$_3$BH also failed. It is worth noting that preparation of a more reactive 1'-O-Tf derivative failed due to the opening of the furanose ring under triflylation conditions.

Pankiewicz et al., (*J. Org. Chem.* 1988, 53, 3473–3479) reported hydrogenolytic opening of the hemiacetal ring of 6-pyridine lactol derivatives to generate mixtures of allo and altro isomers. Reaction of 3 with NaBH$_4$ proceeded in a quantitative yield to give ca 1:1 ratio of allo/altro 7. These epimers were not separated but treated under standard Mitsunobu conditions [diethyl azodicarboxylate (DEAD)/Ph$_3$P/THF, reflux] to give 5 (α/β ratio 1:2) and 3-(2,3-O-isopropylidene-5-O-t-butyidiphenylsilyl-α-L-lyxofuranosyl)-2-fluoropyridine (8), the latter arising from the competitive formation of 4'-oxyphosphonium intermediate. Yokoyama et al., (*Chem. Lett.* 1994, 265–268) speculated that such an intermediate is formed because of the hydrogen bonding between 1'-OH and the hydrogen acceptor on the 2-pyridyl base. It is worth noting that if Mitsunobu cyclization of 7 was conducted at rt more lyxo derivative 8 was obtained than at reflux temperature. This indicates the existence of the hydrogen bond between 1'-OH and fluorine in its close proximity which could be disrupted by increasing the reaction temperature. Recently, an efficient synthesis of imidazole C-nucleosides was reported using similar Mitsunobu cyclization as the key step (Hurusawa et al., *J. Org. Chem.* 1996, 61, 4405–4411). It was difficult to chromatographically separate the mixture of 5 and 8 so it was first 5'-desilylated with TBAF and then fractionated using flash silica gel column chromatography. In a typical procedure 7 (7 g, 13 mmol) and Ph$_3$P (5.25 g, 20 mmol) are dissolved in THF and the mixture is heated to reflux. DEAD (3.15 ml, 20 mmol) is than added to the refluxing mixture and heating continued for 1 hour. Solvent is removed in vacuo and the residue purified by flash column chromatography using 9–11% gradient of ethyl acetate in hexanes for elution. 5.6 g, 83% of the mixture of 5 and 8 was obtained after removal of solvents (see FIG. 8B). The above mixture is dissolved in THF (75 ml) and treated with 1 M TBAF in THF (22 ml, 2 eq) for 1 hour. It is than concentrated in vacuo and chromatographed on the column of silica gel using 15–70% gradient of ethyl acetate in hexanes for elution. α-Anomer 10 eluted first (0.56 g, 19%), followed by β-anomer 9 (1.6 g, 54%). Lyxo derivative 11 eluted last (0.55 g, 19%). β-anomer 9 was obtained in 45% yield in two steps from 7, while α-anomer 10 and lyxo derivative 11 were both obtained in 16% yield. 9 was converted into free 2-fluoro nucleoside 12 (mp 134–135° C., from THF) by boiling in 80% acetic acid and then converted into 2-(benzyloxy) derivative with BnOK ($^1$H NMR (CD$_3$OD) data for 12: δ8.19 (m, 1H, H6), 8.11 (m, 1H, H4), 7.32 (m, 1H, H5), 4.98 (d, $J_{1',2'}$=5.6, 1H, H1'), 4.05–3.96 (m, 3H, H2', H3', H4'), 3.84 (dd, $J_{5',4'}$=3.0, $J_{5',5''}$=12.0, 1H, H5'), 3.73 (dd, $J_{5'',4'}$=4.6, $J_{5'',5'}$=12.0, 1H, H5"). Catalytic hydrogenolysis of benzyl group (H$_2$, Pd—C) simultaneously cleaved C1'-O4' bond. Debenzylation was carried out successfully with trimethylsilyl iodode (TMSI) to afford 3-(β-D-ribofuranosyl)pyridin-2-one (13) in 83% yield as a syrup [UV(MeOH) $\lambda_{max}$ 302 nm]. α-Anomer 10 was deprotected in the same manner as 9 to give 14 (mp 173–174° C., from $CH_2Cl_2$; $^1H$ NMR ($CD_3OD$) data for 14: δ8.12–8.06 (m, 2H, H6,H4), 7.31 (m, 1H, H5), 5.26 (d, $J_{1',2'}$=2.8, 1H, H1'), 4.35–4.25 (m, 2H, H2', H3'), 4.04 (m, 1H, H4'), 3.88 (dd, $J_{5',4'}$=2.6, $J_{5',5''}$=32 11.8, 1H, H5'), 3.68 (dd, $J_{5'',4'}$=4.6, $J_{5'',5'}$=11.8, 1H, H5"). An attempt to displace fluorine in 14 with benzylate yielded the anhydro derivative 15 in a quantitative yield [mp 195–196° C., UV(MeOH) $\lambda_{max}$ 286 nm; $^1$ H NMR $(CD_3)_2CO$ data for 15: δ8.10 (dd, $J_{6,5}$=5.2, $J_{6,4}$=1.6, 1H, H6), 7.80 (dd, $J_{4,5}$=7.3, $J_{4,6}$=1.6, 1H, H4), 6.95 (dd, $J_{5,6}$=5.2, $J_{5,4}$=7.3, 1H, H5), 5.59 (d, $J_{1',2'}$=6.0, 1H, H1'), 5.36 (d, $J_{OH,3'}$=7.2, 1H, 3'OH), 5.02 (dd, $J_{2',3'}$=6.0, $J_{2',3'}$=5.2, 1H, H2'), 4.64 (t, $J_{5',OH}$=5.4, 1H, OH5'), 3.97 (m, 1H, H3'), 3.62 (dq, $J_{5',4'}$=2.2, $J_{5',5''}$=12.2, 1H, H5'), 3.39 (m, 1H, H5"), 3.22 (m, 1H, H4')]. This unexpected cyclization can be explained by an intramolecular nucleophilic displacement of fluorine by an adjacent 2'-hydroxyl. The structure of 11 was confirmed by NOE experiments in which mutual enhancement was observed between H4' and H3' (6% NOE) and between H4' and H4 (5% NOE).

Applicant has now described useful methods for the synthesis of larger guantities of β-anomers of C-nucleosides 12 an 13 as starting materials for the preparation of building blocks for oligonucleotide synthesis. These analogs are also interesting as potential antiviral and/or anticancer agents.

Example 4

Synthesis of 1-(5-O-Dimethoxytrityl-2-O-tert-butyidimethylsilyl-3-O-2-cyanoethyl-N,N-diisopropylaminophosphoramidite-β-D-Ribofuranosyl)-1,4-dihydro-pyrimidine-4-one (7)

Referring to FIG. 9, 1-(2,3,5-Tri-O-benzoyl-β-D-ribofuranosyl)-1,4-dihydropyrimidine-4-one (3) was synthesized in accordance with Niedballa et al., *J. Org. Chem* 1974, 39, 3668–3671. 1-(β-D-Ribofuranosyl)-1,4-dihydropyrimidine-4-one (5) was prepared by standard NaOMe/MeOH deprotection of derivative 3 with nearly quantitative yield. 1-(5-O-Dimethoxytrityl-β-D-Ribofuranosyl)-1,4-dihydropyrimidine-4-one (6) was prepared by standard dimethoxytritylation of 5 in pyridine (rt., overnight) resulting in a yield of 83%. 1-(5-O-Dimethoxytrityl-2-O-tert-butyldimethylsilyl-β-D-Ribofuranosyl)-1,4-dihydropyrimidine-4-one was prepared using standard silylation procedure (Hakimelahi et al., *Can. J. Chem.* 1982, 60, 1106–1113). 1-[5-O-Dimethoxytrityl-2-O-tert-butyidimethylsilyl-3-O-2cyanoethyl-N,N-diisopropylaminophosphoramidite-β-D-Ribofuranosyl]-1,4-dihydro-pyrimidine-4-one (7) was prepared by phosphitylation using standard phosphitylation procedure (Tuschl et al., *Biochemistry* 1993, 32, 11658–11668).

Example 5

Synthesis of 1-(5-O-Dimethoxytrityl-2-O-tert-butyidimethylsilyl-3-O-2-cyanoethyl-N,N-diisopropylaminophosphoramidite-β-D-Ribofuranosyl)-1,4-dihydropyrimidine-2-one (6)

Referring to FIG. 10, compound 6 was prepared as described in Murray et al., *Biochem.J.* 1995, 311, 487–494.

Example 6

Synthesis of 5'-O-Dimethoxytrityl-2'-O-tert-Butyldimethylsilyl-$O^4$-Diphenylcarbamoyl-3-Deaza Uridine 3'-(2-Cyanoethyl N,N-diisopropyl phosphoramidite) (5)

Referring to FIG. 11, compound (5) was prepared as described in U.S. Pat. No. 5,134,066, except for dimethoxytritylation of $O^4$-Diphenylcarbamoyl-3-deaza-uridine (2). The procedure disclosed in the above-mentioned patent afforded desired 5'-O-Dimethoxytrityl-$O^4$-Diphenylcarbamoyl-3-deaza-uridine (3) in only 10% yield. Therefore the following procedure for dimethoxytritylation of 2 was developed.

To the solution of compound 2 (1.95 g, 4.45 mmol) in dichloromethane (60 mL), symm-collidine (1.53 mL, 11.6 mmol) was added followed by the addition of silver nitrate (0.99 g, 5.8 mmol). After stirring at room temperature for 10 min, dimethoxytrityl chloride was added and the reaction mixture was stirred for additional 1 h. Then it was quenched with MeOH (15 mL) and evaporated to dryness. The residue was dissolved in dichloromethane, washed with saturated aq sodium bicarbonate and brine. Organic layer was dried over sodium sulfate and the solvent removed in vacuum. The oily residue was purified by flash chromatography on silica using gradient of EtOAc in Hexanes (30% to 50%) as an eluent to give 3 g (88.8%) of the derivative 3.

Example 7

Synthesis of 2-O-t-Butyldimethylsilyl-5-O-Dimethoxytrityl-3-O-(2-Cyanoethyl-N,N-diisopropylphosphoramidite)-β-D-ribofuranosylindole Referring to FIG. 13, 1-(2,3,5-Tri-O-benzoyl-β-D-ribofuranosyl) indole (2) was synthesized from indole and 2,3,5-tri-O--benzoyl-β-D-ribofuranose (1) according to the procedure of Szarek et al., *Chem.Comm.* 1975, 648–649). 5-O-dimethoxytrityl β-D-ribofuranozylindole (3) was prepared from intermediate 2 by standard deprotection (NaOMe/MeOH) followed by tritylation (DMTCI/Py). 2-O-t-Butyidimethylsilyl-5-O-dimethoxytrityl β-D-ribofuranozylindole (4) was prepared from intermediate 3 by standard silylation (32% yield). 2-O-t-Butyldimethylsilyl-5-O-dimethoxytrityl-3-O-(2-cyanoethyl-N,N-diisopropylphosphoramidite)-β-D-ribofuranozylindole (5) was prepared from intermediate 4 by 3'-O-phosphitylation (85% yield).

Example 8

Synthesis of 2-O-t-Butyidimethylsilyl-5-O-Dimethoxytrityl-3-O-(2-Cyanoethyl-N,N-diisopropylphosphoramidite)-β-D-ribofuranosyl benzimidazole Referring to FIG. 14, 1-(2,3,5-Tri-O-benzoyl-β-D-ribofuranosyl)benzimidazole (2) was synthesized from benzimidazole and 1-O-acetyl-2,3,5-tri-O--benzoyl-β-D-ribofuranose (1) according to the procedure of Kazimierczuk et al., *Naturforsch.* 1980, 35c , 30–35. 5'-O-dimethoxytrityl β-D-ribofuranozyl benzimidazole (3) was prepared from intermediate 2 by standard deprotection (NaOMe/MeOH) followed by tritylation (DMTCI/Py). 2'-O-t-Butyidimethylsilyl-5'-O-dimethoxytrityl β-D-ribofuranozyl benzimidazole (4) was prepared from intermediate 3 by standard silylation (32% yield). 2'-O-t-Butyldimethylsilyl-5'-O-dimethoxytrityl-3-O-(2-cyanoethyl-N,N-diisopropylphosphoramidite)-β-D-ribofuranozyl benzimidazole (5) was prepared from intermediate 4 by 3'-O-phosphitylation (85% yield).

Example 9

Synthesis of 3-(β-D-Ribofuranosyl)-Pyridine-2-(4-Nitrophenylethyl)-One and 5-(δ-D-Ribofuranosyl)-Pyridine-2-(4-Nitrophenylethyl)-One Phosphoramidite Referring to FIG. 15, treatment of 3-(β-D-Ribofuranosyl)-pyridin-2-one (1 in FIG. 6) with TBDMSi-Cl/DMF, NPEOH/Ph3P/DEAD/THF, and TFA, CHCl3, will yield 3-(β-D-Ribofuranosyl)-pyridin-2-(4-nitrophenylethyl)-one (7).

Treatment of 5-(β-D-Ribofuranosyl)-pyridin-2-one (2 in FIG. 6) with TBDMSi-Cl/DMF, NPEOH/Ph3P/DEAD/THF, and TFA, CHCl3, will yield 5-(β-D-Ribofuranosyl)-pyridin-2-(4-nitrophenylethyl)-one (8).

Both compounds 7 and 8 is readily converted into phosphoramidites using the standard protocols described above.

Phosphoramidites of the novel anologs of the instant invention are incorporated into polynucleotides using the method of synthesis, deprotection, purification and testing previously described (Wincott et al., 1995 supra).

Example 10

4-Benzylamino-1H-pyridine-2-one or $N^4$-benzyl-3-deaza cytosine

Title compound was prepared from 4-hydroxy-1H-pyridin-2-one (1) as described in Hung, N. C.; Bisagni, E. *Synthesis,* 1984, 765.

4-Benzylamino-1-(2,3,5-tri-O-benzoyl-β-D-ribofuranosyl)-1H-pyridin-2-one (3) or $N^4$-benzyl-2',3',5'-tri-O-benzoyl-3-deaza cytidine: The suspension of 2 (2.8 g, 14.0 mmol) in the mixture of hexamethyldisilazane (50 mL) and trimethylchlorosilane (5 mL) was refluxed for three hours. The resulting clear solution of trimethylsilyl derivative of 2 was evaporated to dryness. To the solution of the resulting clear oil in dry acetonitrile (40 mL), 1-O-acetyl-2,3,5-tri-O-benzoyl-D-ribofuranose (7.06 g, 14.7 mmol) was added and the reaction mixture was cooled to 0° C. To the above stirred solution trimethylsilyl trifluoromethanesulfonate (3.25 mL, 16.8 mmol) was added drop-wise and the reaction mixture was allowed to warm to a room temperature and left overnight. After that the reaction mixture was diluted with dichloromethane washed with saturated sodium bicarbonate. The precipitate of the unreacted 2, was isolated by filtration. Then layers were separated and organic layer washed with brine and evaporated. The residue was purified by flash chromatography on silica gel to give 5.5 g (60%) of the compound 3.

4-Amino-1-(2,3,5-tri-O-benzoyl-β-D-ribofuranosyl)-1H-pyridin-2-one (4) or 2',3',5'-tri-O-benzoyl-3-deaza cytidine: Compound 4 is prepared by catalytic hydrogenolysis (Pd/C) of 3 in ethanol at room temperature.

4-Acetylamino-1-(2,3,5-tri-O-benzoyl-β-D-ribofuranosyl)-1H-pyridin-2-one (5): Compound 5 is prepared by standard acetylation of the derivative 4 with acetic anhydride in pyridine.

4-Acetylamino-1-(β-D-ribofuranosyl)-1H-pyridin-2-one (6): The title compound is prepared by selective deprotection of sugar moiety of derivative 5 with 2M aq NaOH in pyridine-ethanol mixture at −10° C.

4-Acetylamino-1-(5-O-dimethoxytrityl-β-D-ribofuranosyl)-1H-pyridin-2-one (7): compound 7 is prepared using standard protocols described above.

RNA Cleavage Assay in vitro

Substrate RNA is 5' end-labeled using [γ-$^{32}$P] ATP and T4 polynucleotide kinase (U.S. Biochemicals). Cleavage reactions are carried out under ribozyme "excess" conditions. Trace amount (≦1 nM) of 5' end-labeled substrate and 40 nM unlabeled ribozyme are denatured and renatured separately by heating to 90° C. for 2 min and snap-cooling on ice for 10–15 min. The ribozyme and substrate are incubated, separately, at 37° C. for 10 min in a buffer containing 50 mM Tris-HCl and 10 mM MgCl$_2$. The reaction is initiated by mixing the ribozyme and substrate solutions and incubating at 37° C. Aliquots of 5 μl are taken at regular intervals of time and the reaction is quenched by mixing with equal volume of 2×formamide stop mix. The samples are resolved on 20% denaturing polyacrylamide gels. The results are quantified and percentage of target RNA cleaved is plotted as a function of time.

Diagnostic Uses

Ribozymes of this invention may be used as diagnostic tools to examine genetic drift and mutations within diseased cells or to detect the presence of a specific RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE 1

Characteristics of Naturally Occurring Ribozymes
Group I Introns
Size: ~150 to >1000 nucleotides.
Requires a U in the target sequence immediately 5' of the cleavage site.
Binds 4–6 nucleotides at the 5'-side of the cleavage site.

Reaction mechanism: attack by the 3'-OH of guanosine to generate cleavage products with 3'-OH and 5'-guanosine.
Additional protein cofactors required in some cases to help folding and maintenance of the active structure [1].
Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [2,3].
Complete kinetic framework established for one ribozyme [4,5,6,7].
Studies of ribozyme folding and substrate docking underway [8,9,10].
Chemical modification investigation of important residues well established [11,12].
The small (4–6 nt) binding site may make this ribozyme too non-specific for targeted RNA cleavage, however, the Tetrahymena group I intron has been used to repair a "defective" β-galactosidase message by the ligation of new β-galactosidase sequences onto the defective message [13].

RNAse P RNA (M1 RNA)
Size: ~290 to 400 nucleotides.
RNA portion of a ubiquitous ribonucleoprotein enzyme.
Cleaves tRNA precursors to form mature tRNA [14].
Reaction mechanism: possible attack by $M^{2+}$—OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P for therapeutic applications is possible through hybridization of an External Guide Sequence (EGS) to the target RNA [15,16]
Important phosphate and 2' OH contacts recently identified [17,18]

Group II Introns
Size: >1000 nucleotides.
Trans cleavage of target RNAs recently demonstrated [19, 20].
Sequence requirements not fully determined.
Reaction mechanism: 2'-OH of an internal adenosine generates cleavage products with 3'-OH and a "lariat" RNA containing a 3'–5' and a 2'–5' branch point.
Only natural ribozyme with demonstrated participation in DNA cleavage [21,22] in addition to RNA cleavage and ligation.
Major structural features largely established through phylogenetic comparisons [23].
Important 2' OH contacts beginning to be identified [24]
Kinetic framework under development [25]

Neurospora VS RNA
Size: ~144 nucleotides.
Trans cleavage of hairpin target RNAs recently demonstrated [26].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.

Hammerhead Ribozyme
(see text for references)
Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissile bond to generate cleavage products with 2',3'-cyclic phosphate and 5'-OH ends.
14 known members of this class. Found in a number of plant pathogens (virusoids) that use RNA as the infectious agent.
Essential structural features largely defined, including 2 crystal structures [ ]
Minimal ligation activity demonstrated (for engineering through in vitro selection) [ ]
Complete kinetic framework established for two or more ribozymes [ ].
Chemical modification investigation of important residues well established [ ].

Hairpin Ribozyme
Size: ~50 nucleotides.
Requires the target sequence GUC immediately 3' of the cleavage site.
Binds 4–6 nucleotides at the 5'-side of the cleavage site and a variable number to the 3'-side of the cleavage site.
Reaction mechanism: attack by 2'-OH 5' to the scissile bond to generate cleavage products with 2',3'-cyclic phosphate and 5'-OH ends.
3 known members of this class. Found in three plant pathogen (satellite RNAs of the tobacco ringspot virus, arabis mosaic virus and chicory yellow mottle virus) which uses RNA as the infectious agent.
Essential structural features largely defined [27,28,29,30]
Ligation activity (in addition to cleavage activity) makes ribozyme amenable to engineering through in vitro selection [31]
Complete kinetic framework established for one ribozyme [32].
Chemical modification investigation of important residues begun [33,34].

Hepatitis Delta Virus (HDV) Ribozyme
Size: ~60 nucleotides.
Trans cleavage of target RNAs demonstrated [35].
Binding sites and structural requirements not fully determined, although no sequences 5' of cleavage site are required. Folded ribozyme contains a pseudoknot structure [36].
Reaction mechanism: attack by 2'-OH 5' to the scissile bond to generate cleavage products with 2',3'-cyclic phosphate and 5'-OH ends.
Only 2 known members of his class. Found in human HDV. Circular form of HDV is active and shows increased nuclease stability [37].

1. Mohr, G.; Caprara, M. G.; Guo, Q.; Lambowitz, A. M. Nature, 370, 147–150 (1994).
2. Michel, Francois; Westhof, Eric. Slippery substrates. Nat. Struct. Biol. (1994), 1(1), 5–7.
3. Lisacek, Frederique; Diaz, Yolande; Michel, Francois. Automatic identification of group I intron cores in genomic DNA sequences. J. Mol. Biol. (1994), 235(4), 1206–17.
4. Herschlag, Daniel; Cech, Thomas R., Catalysis of RNA cleavage by the *Tetrahymena thermophila* ribozyme. 1. Kinetic description of the reaction of an RNA substrate complementary to the active site. Biochemistry (1990), 29(44), 10159–71.
5. Herschlag, Daniel; Cech, Thomas R., Catalysis of RNA cleavage by the *Tetrahymena thermophila* ribozyme. 2. Kinetic description of the reaction of an RNA substrate that forms a mismatch at the active site. Biochemistry (1990), 29(44), 10172–80.
6. Knitt, Deborah S.; Herschlag, Daniel. pH Dependencies of the Tetrahymena Ribozyme Reveal an Unconventional Origin of an Apparent pKa. Biochemistry (1996), 35(5), 1560–70.
7. Bevilacqua, Philip C.; Sugimoto, Naoki; Turner, Douglas H., A mechanistic framework for the second step of splicing catalyzed by the Tetrahymena ribozyme. Biochemistry (1996), 35(2), 648–58.
8. Li, Yi; Bevilacqua, Philip C.; Mathews, David; Turner, Douglas H., Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.
9. Banerjee, Aloke Raj; Turner, Douglas H., The time dependence of chemical modification reveals slow steps in the folding of a group I ribozyme. Biochemistry (1995), 34(19), 6504–12.
10. Zarrinkar, Patrick P.; Williamson, James R., The P9.1–P9.2 peripheral extension helps guide folding of the Tetrahymena ribozyme. Nucleic Acids Res. (1996), 24(5), 854–8.
11. Strobel, Scott A.; Cech, Thomas R., Minor groove recognition of the conserved G.cntdot.U pair at the Tetrahymena ribozyme reaction site. Science (Washington, D.C.) (1995), 267(5198), 675–9.
12. Strobel, Scott A.; Cech, Thomas R. Exocyclic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201–11.
13. Sullenger, Bruce A.; Cech, Thomas R., Ribozyme-mediated repair of defective mRNA by targeted trans-splicing. Nature (London) (1994), 371(6498), 619–22.
14. Robertson, H. D.; Altman, S.; Smith, J. D. J. Biol. Chem., 247, 5243–5251 (1972).
15. Forster, Anthony C.; Altman, Sidney. External guide sequences for an RNA enzyme. Science (Washington, D.C., 1883-) (1990), 249(4970), 783–6.
16. Yuan, Y.; Hwang, E. S.; Altman, S. Targeted cleavage of mRNA by human RNase P. Proc. Natl. Acad. Sci. USA (1992) 89, 8006–10.
17. Harris, Michael E.; Pace, Norman R. Identification of phosphates involved in catalysis by the ribozyme RNase P RNA. RNA (1995), 1(2), 210–18.
18. Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510–14.
19. Pyle, Anna Marie; Green, Justin B., Building a Kinetic Framework for Group II Intron Ribozyme Activity: Quantitation of Interdomain Binding and Reaction Rate. Biochemistry (1994), 33(9), 2716–25.
20. Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.
21. Zimmerly, Steven; Guo, Huatao; Eskes, Robert; Yang, Jian; Perlman, Philip S.; Lambowitz, Alan M., A group II intron RNA is a catalytic component of a DNA endonuclease involved in intron mobility. Cell (Cambridge, Mass.) (1995), 83(4), 529–38.
22. Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761–70.
23. Michel, Francois; Ferat, Jean Luc. Structure and activities of group II introns. Annu. Rev. Biochem. (1995), 64, 435–61.
24. Abramovitz, Dana L.; Friedman, Richard A.; Pyle, Anna Marie. Catalytic role of 2'-hydroxyl groups within a group II intron active site. Science (Washington, D.C.) (1996), 271(5254), 1410–13.
25. Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256(1), 31–49.
26. Guo, Hans C. T.; Collins, Richard A., Efficient trans-cleavage of a stem-loop RNA substrate by a ribozyme derived from Neurospora VS RNA. EMBO J. (1995), 14(2), 368–76.
27. Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299–304.
28. Chowrira, Bharat M.; Berzal-Herranz, Alfredo; Burke, John M., Novel guanosine requirement for catalysis by the hairpin ribozyme. Nature (London) (1991), 354 (6351), 320–2.
29. Berzal-Herranz, Alfredo; Joseph, Simpson; Chowrira, Bharat M.; Butcher, Samuel E.; Burke, John M., Essential nucleotide sequences and secondary structure elements of the hairpin ribozyme. EMBO J. (1993), 12(6), 2567–73.
30. Joseph, Simpson; Berzal-Herranz, Alfredo; Chowrira, Bharat M.; Butcher, Samuel E., Substrate selection rules for the hairpin ribozyme determined by in vitro selection, mutation, and analysis of mismatched substrates. Genes Dev. (1993), 7(1), 130–8.
31. Berzal-Herranz, Alfredo; Joseph, Simpson; Burke, John M., In vitro selection of active hairpin ribozymes by sequential RNA-catalyzed cleavage and ligation reactions. Genes Dev. (1992), 6(1), 129–34.
32. Hegg, Lisa A.; Fedor, Martha J., Kinetics and Thermodynamics of Intermolecular Catalysis by Hairpin Ribozymes. Biochemistry (1995), 34(48), 15813–28.
33. Grasby, Jane A.; Mersmann, Karin; Singh, Mohinder; Gait, Michael J., Purine Functional Groups in Essential Residues of the Hairpin Ribozyme Required for Catalytic Cleavage of RNA. Biochemistry (1995), 34(12), 4068–76.
34. Schmidt, Sabine; Beigelman, Leonid; Karpeisky, Alexander; Usman, Nassim; Sorensen, Ulrik S.; Gait, Michael J., Base and sugar requirements for RNA cleavage of essential nucleoside residues in internal loop B of the hairpin ribozyme: implications for secondary structure. Nucleic Acids Res. (1996), 24(4), 573–81.
35. Perrotta, Anne T.; Been, Michael D., Cleavage of oligoribonucleotides by a ribozyme derived from the hepatitis.delta.virus RNA sequence. Biochemistry (1992), 31(1), 16–21.
36. Perrotta, Anne T.; Been, Michael D., A pseudoknot-like structure required for efficient self-cleavage of hepatitis delta virus RNA. Nature (London) (1991), 350(6317), 434–6.
37. Puttaraju, M.; Perrotta, Anne T.; Been, Michael D., A circular trans-acting hepatitis delta virus ribozyme. Nucleic Acids Res. (1993), 21(18), 4253–8.

TABLE 2

| 2.5 μmol RNA Synthesis Cycle | | | |
|---|---|---|---|
| Reagent | Equivalents | Amount | Wait Time* |
| Phosphoramidites | 6.5 | 163 μL | 2.5 |
| S-Ethyl Tetrazole | 23.8 | 238 μL | 2.5 |
| Acetic Anhydride | 100 | 233 μL | 5 sec |
| N-Methyl Imidazole | 186 | 233 μL | 5 sec |
| TCA | 83.2 | 1.73 mL | 21 sec |
| Iodine | 8.0 | 1.18 mL | 45 sec |
| Acetonitrile | NA | 6.67 mL | NA |

*Wait time does not include contact time during delivery.

What is claimed is:

1. A nucleoside or a nucleotide compound comprising a nucleic acid base portion, wherein said base is selected from a group consisting of 2-fluoropyridine-3-yl, pyridine-2-one-3-yl; pyridin-2-(4-nitrophenylethyl)-one-3-yl, 2-bromopyridine-5-yl, 2-bromopyridine-5-yl, pyridin-2-one-5-yl, 2-aminopyridine-5-yl, and pyridin-2-(4-nitrophenylethyl)-one-5-yl.

2. A compound having the formula I:

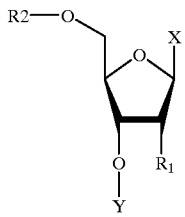

wherein, $R_1$ is independently H; OH; O—$R_3$, where $R_3$ is independently a moiety selected from the group consisting of alkyl, alkenyl, alkynyl, aryl, alkylaryl, carbocyclic aryl, heterocyclic aryl, amide and ester; C—$R_3$, where $R_3$ is independently a moiety selected from a group consisting of alkyl, alkenyl, alkynyl, aryl, alkylaryl, carbocyclic aryl, heterocyclic aryl, amide and ester; halo; $NHR_4$, wherein $R_4$ is a moiety selected from the group consisting of a C1–22 alkyl group, a C1–22 acyl group, a substituted or unsubstituted aryl; or $OCH_2SCH_3$, wherein said substituted aryl is substituted with one or more substituents selected from the group consisting of halogen, trihalomethyl, hydroxyl, SH, cyano, alkoxy, alkyl, alkenyl, alkynyl, and amino groups;

X is independently a nucleotide base selected from the group consisting of 2-fluoropyridine-3-yl, pyridine-2-one-3-yl; pyridin-2-(4-nitrophenylethyl)-one-3-yl, 2-bromopyridine-5-yl, 2-bromopyridine-5-yl, pyridin-2-one-5-yl, 2-aminopyridine-5-yl, and pyridin-2-(4-nitrophenylethyl)-one-5-yl;

Y is independently a phosphorus-containing group; and

R2 is independently a blocking group or a phosphorus-containing group.

3. A compound having the formula II:

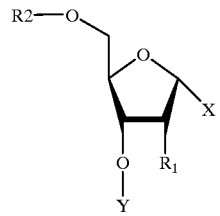

wherein, $R_1$ is independently H; OH; O—$R_3$, where $R_3$ is independently a moiety selected from the group consisting of alkyl, alkenyl, alkynyl, aryl, alkylaryl, carbocyclic aryl, heterocyclic aryl, amide and ester; C—$R_3$, where $R_3$ is independently a compound selected from a group consisting of alkyl, alkenyl, alkynyl, aryl, alkylaryl, carbocyclic aryl, heterocyclic aryl, amide and ester; halo; $NHR_4$, where $R_4$ is selected from the group consisting of a C1–22 alkyl group, a C1–22 acyl group, or substituted or unsubstituted aryl; or $OCH_2SCH_3$, wherein said substituted aryl is substituted with one or more substituents selected from the group consisting of halogen, trihalomethyl, hydroxyl, SH, cyano, alkoxy, alkyl, alkenyl, alkynyl, and amino groups;

X is independently a nucleotide base selected from the group consisting of 2-fluoropyridine-3-yl, 2-bromopyridine-5-yl, pyridin-2-one-5-yl, and 2-aminopyridine-5-yl;

Y is independently a phosphorus-containing group; and

R2 is independently a blocking group or a phosphorus-containing group.

4. The compound of claim 1, wherein said compound is a nucleotide.

5. The compound of claim 1, wherein said compound is a nucleotide-tri-phosphate.

6. The compound of claim 2, wherein said compound is 3-(β-D-Ribofuranosyl)-2-fluoropyridine.

7. The compound of claim 2, wherein said compound is 3-(β-D-Ribofuranosyl)-pyridin-2-one.

8. The compound of claim 2, wherein said compound is 3-(β-D-Ribofuranosyl)-pyridin-2-(4-nitrophenylethyl)-one.

9. The compound of claim 3, wherein said compound is 3-(α-D-ribofuranosyl)-2-fluoropyridine.

10. The compound of claim 2, wherein said compound is 5-(β-D-ribofuranosyl)-2-bromopyridine.

11. The compound of claim 3, wherein said compound is 5-(α-D-ribofuranosyl)-2-bromopyridine.

12. The compound of claim 2, wherein said compound is 5-(β-D-ribofuranosyl)-pyridin-2-one.

13. The compound of claim 3, wherein said compound is 5-(α-D-ribofuranosyl)-pyridin-2-one.

14. The compound of claim 2, wherein said compound is 5-(β-D-ribofuranosyl)-2-aminopyridine.

15. The compound of claim 2, wherein said compound is 5-(β-D-ribofuranosyl)-pyridin-2-(4-nitrophenylethyl)-one.

16. The compound of claim 3, wherein said compound is 5-(α-D-ribofuranosyl)-2-aminopyridine.

\* \* \* \* \*